US009078638B2

(12) United States Patent
Wuestemann et al.

(10) Patent No.: US 9,078,638 B2
(45) Date of Patent: Jul. 14, 2015

(54) BONE MARROW ASPIRATOR AND METHODS THEREFOR

(75) Inventors: Thies Wuestemann, Nyack, NY (US);
Michael D. Lynch, Ramsey, NJ (US);
Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1548 days.

(21) Appl. No.: 12/572,442

(22) Filed: Oct. 2, 2009

(65) Prior Publication Data
US 2011/0082425 A1 Apr. 7, 2011

(51) Int. Cl.
*A61B 10/02* (2006.01)

(52) U.S. Cl.
CPC .......... *A61B 10/025* (2013.01); *A61B 10/0283* (2013.01); *A61B 2010/0258* (2013.01)

(58) Field of Classification Search
CPC ............ A61B 10/025; A61B 10/0283; A61B 2010/0258
USPC ......................... 600/563, 567–568, 564, 562; 604/117–121; 606/171
See application file for complete search history.

(56) References Cited

U.S. PATENT DOCUMENTS

| | | | |
|---|---|---|---|
| 493,730 A | 3/1893 | MacKensie | |
| 4,036,232 A | 7/1977 | Genese | |
| 4,287,819 A | 9/1981 | Emerit | |
| 4,366,822 A | 1/1983 | Altshuler | |
| 4,373,535 A | 2/1983 | Martell | |
| 4,461,305 A | 7/1984 | Cibley | |
| 4,660,569 A | 4/1987 | Etherington | |
| 4,732,162 A | 3/1988 | Martell | |
| 5,241,969 A | 9/1993 | Carson et al. | |
| 5,257,632 A | 11/1993 | Turkel et al. | |
| 5,324,300 A | 6/1994 | Elias et al. | |
| 5,634,473 A | 6/1997 | Goldenberg et al. | |
| 5,713,368 A | 2/1998 | Leigh | |
| 5,779,647 A | 7/1998 | Chau et al. | |
| 5,830,152 A | 11/1998 | Tao | |
| 6,702,760 B2 * | 3/2004 | Krause et al. | 600/564 |
| 6,730,043 B2 | 5/2004 | Krueger et al. | |
| 6,916,292 B2 | 7/2005 | Morawski et al. | |
| 7,081,123 B2 | 7/2006 | Merboth et al. | |
| 7,207,951 B1 | 4/2007 | Lurie et al. | |
| 7,226,424 B2 * | 6/2007 | Ritchart et al. | 600/566 |

(Continued)

OTHER PUBLICATIONS

Muschler et al., JBJS 79:1699-1709, 1997.

(Continued)

*Primary Examiner* — Nicholas Lucchesi
*Assistant Examiner* — Weng Lee
(74) *Attorney, Agent, or Firm* — Lerner, David, Littenberg, Krumholz & Mentlik, LLP

(57) ABSTRACT

A device and method for aspirating fluid from a body cavity are disclosed herein. The device disclosed utilizes a reservoir in fluid communication with a needle via a tube connected to a pump. The needle is able to displace a desired distance. Further, the aspirator includes a selector switch capable having three positions. In the first position anticoagulant is pumped through the system. In the second position bone marrow is aspirated but the needle is not moved. In the third position the displacement of the needle is controlled as well as the volume in the reservoir. Further, in the third position, the volume in the reservoir and the needle displacement are proportional to one another.

19 Claims, 22 Drawing Sheets

(56) References Cited

U.S. PATENT DOCUMENTS

| | | |
|---|---|---|
| 7,278,972 B2 | 10/2007 | Lamoureux et al. |
| 7,462,181 B2 * | 12/2008 | Kraft et al. .................... 606/96 |
| 2003/0208181 A1 | 11/2003 | Geise et al. |
| 2003/0225344 A1 | 12/2003 | Miller |
| 2004/0127814 A1 | 7/2004 | Negroni |
| 2004/0153005 A1 | 8/2004 | Krueger |
| 2004/0191897 A1 * | 9/2004 | Muschler .................... 435/325 |
| 2004/0215102 A1 | 10/2004 | Ikehara et al. |
| 2005/0096627 A1 | 5/2005 | Howard |
| 2006/0167379 A1 | 7/2006 | Miller |
| 2008/0045861 A1 | 2/2008 | Miller et al. |
| 2008/0045965 A1 | 2/2008 | Miller et al. |
| 2008/0071193 A1 | 3/2008 | Reuber et al. |

OTHER PUBLICATIONS

Synthes, The Answer to Bone Voids, 2006.

* cited by examiner

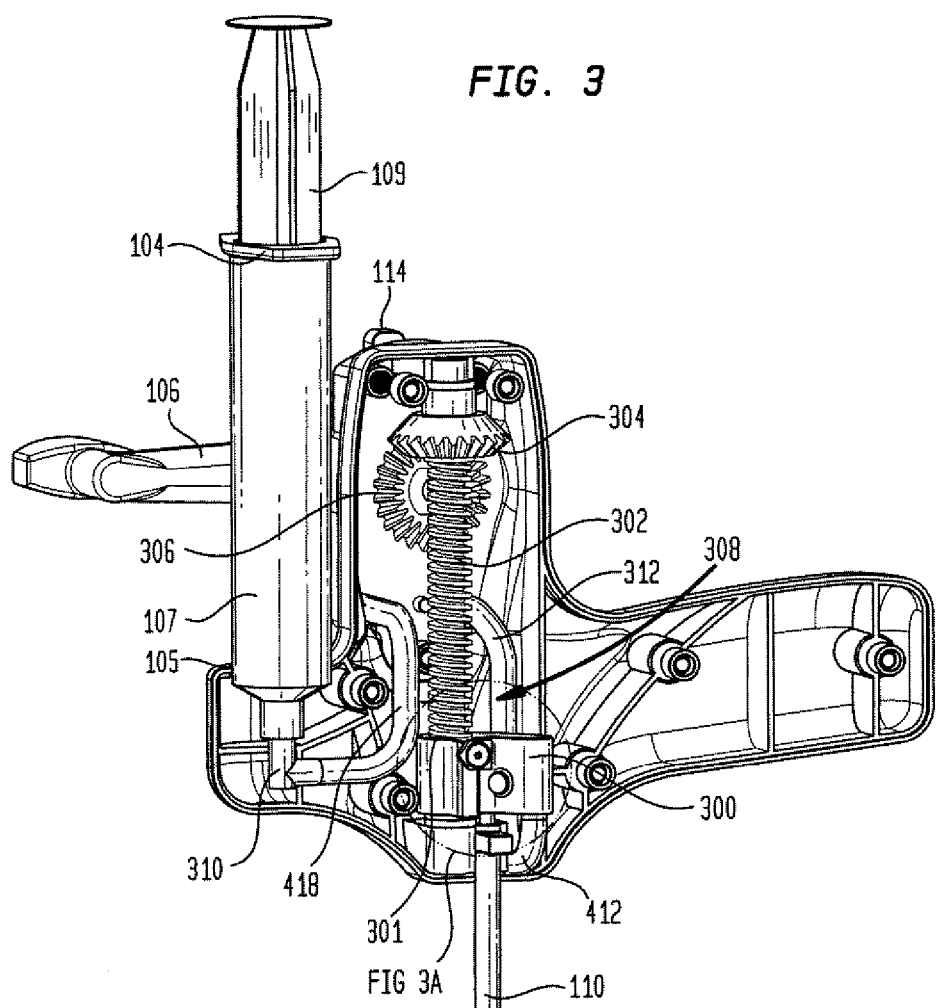
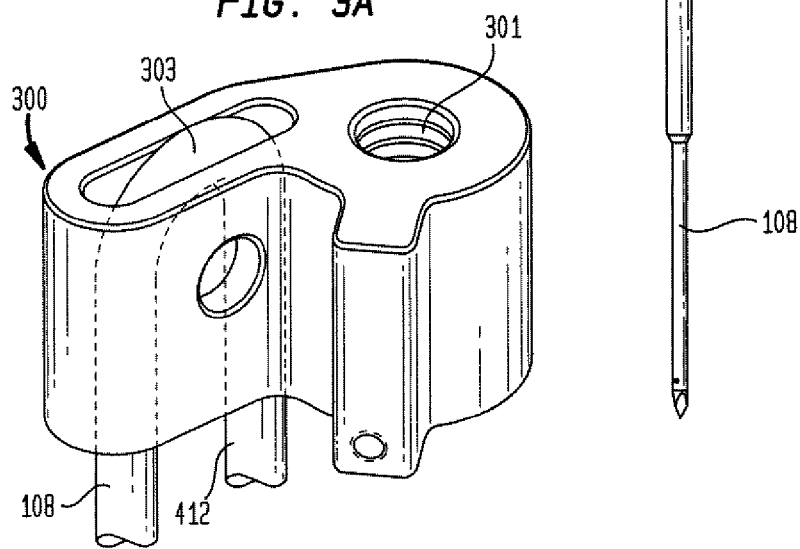

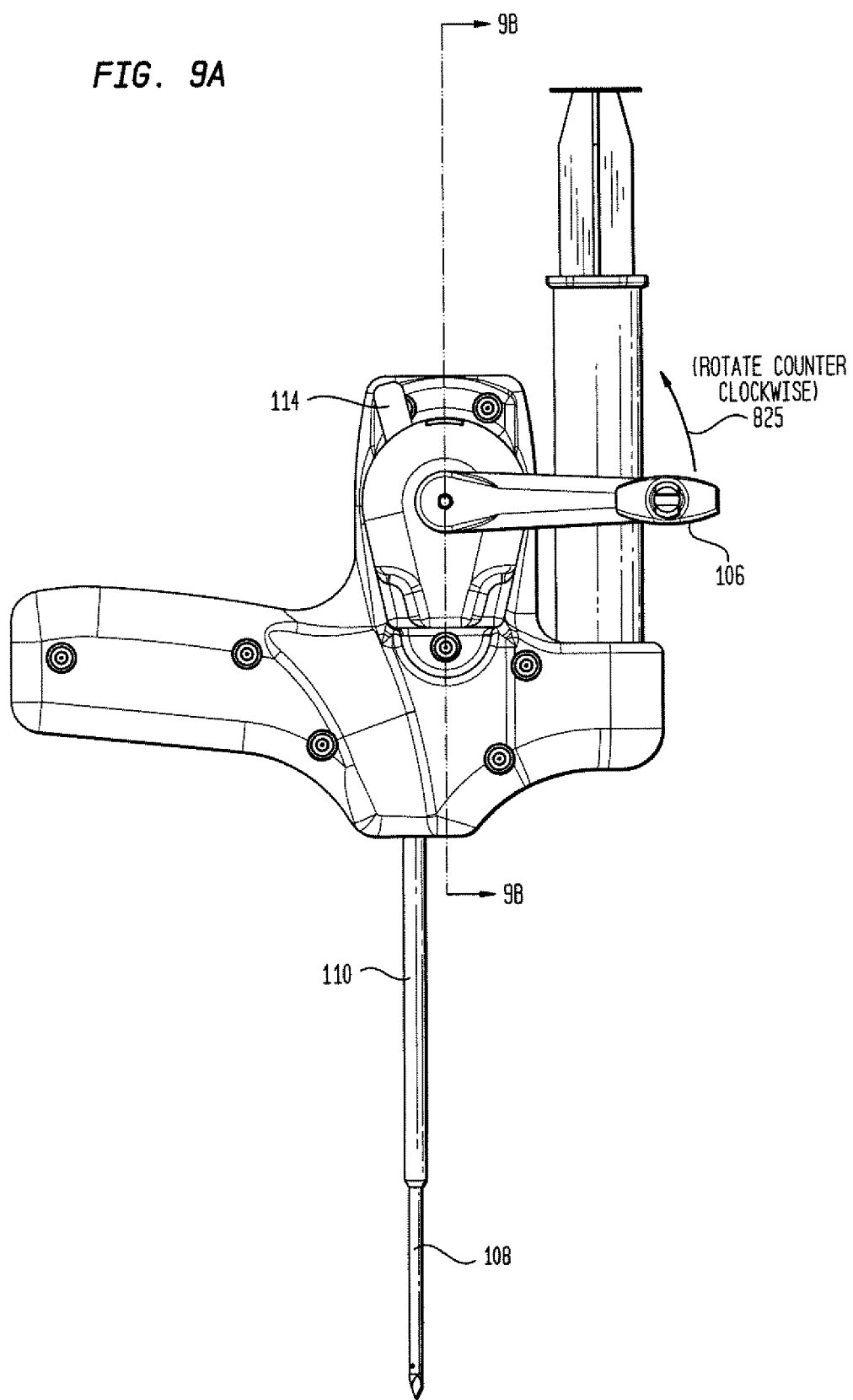

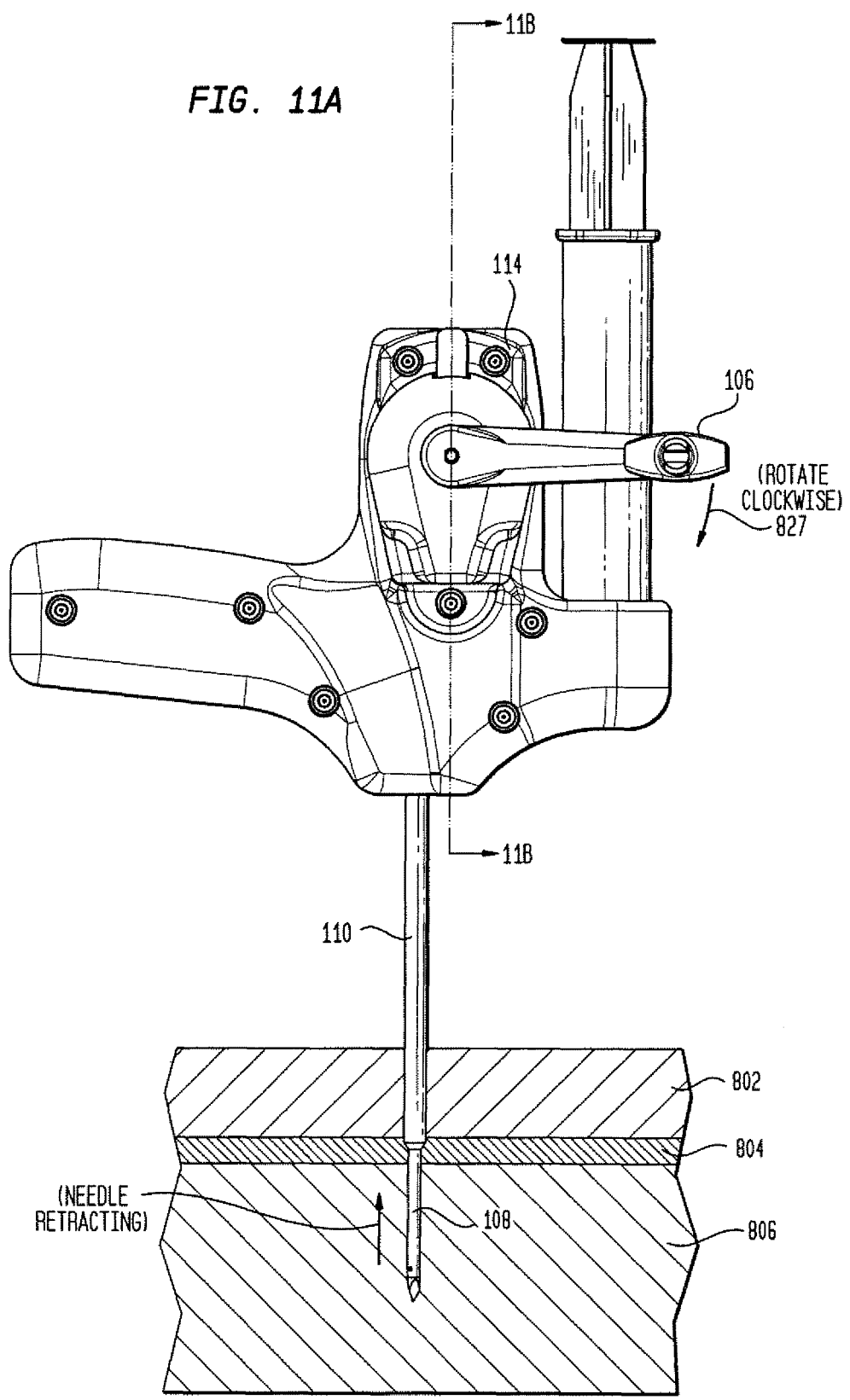

BONE MARROW ASPIRATOR AND METHODS THEREFOR

BACKGROUND OF THE INVENTION

The present invention is directed to a bone marrow aspirator and methods of use thereof.

Numerous medical conditions require extracting bone marrow from a patient. Such conditions include, but are not limited to, leukemias, brain tumors, breast cancer, hodgkin's disease, neuroblastoma, and ovarian cancer. Further, a wide spectrum of procedures require bone marrow. For example, bone marrow may be needed for spinal fusion, non-union fractures, revisions of total hip and knee arthroplasty procedures in which severe bone marrow loss is encountered, as well as numerous other procedures. Further still, some diagnostic tests require samples of bone marrow. For example, marrow samples may be needed to better understand the cause of abnormal blood test results, confirm a diagnosis or check the status of severe anemia of unknown cause, evaluate abnormalities in the blood's ability to store iron, diagnose infection, or marrow samples may be needed for numerous other tests.

Typically, bone marrow is extracted from the patient's iliac crest. To extract marrow, a needle is passed through the soft tissue and cortical bone of a patient and pushed into the cancellous bone. In the cancellous bone, bone marrow is extracted through the needle. The current techniques typically involve penetrating numerous sites in the bone until enough bone marrow is extracted to either treat the condition, perform the procedure, or complete the test.

A current method of aspirating bone marrow consists of driving a needle connected to a syringe into either the anterior or posterior regions of the iliac to a depth relatively proximal i.e. (closest to the cortical surface). As the plunger of the syringe is retracted to generate the necessary vacuum required for aspiration, the needle is slowly rotated 360° in order to collect marrow from a circumferential region about the tip of the needle. Enabling this circumferential collection is a needle that has a side port on its wall adjacent to the tip, and a closed, pointed tip. Upon full collection of marrow at that site, the needle is driven more distally (i.e. deeper) and coupled to a new syringe and the process repeated again. A third depth may be used providing the patient's anatomy is large enough to accommodate the length of the needle without perforating through the distal wall of the iliac crest.

The reason the needle is rotated during aspiration at multiple depths is that bone marrow does not flow easily due to its viscosity and bone to the adjacent trabecular structures. Unlike blood which can flow easily from areas remote to the injection site through capillary action, marrow can only be collected from the general vicinity of the port of the needle. Once that limited marrow space is evacuated, peripheral blood will rush in and flow into the syringe. This is not desirable since the blood will dilute the concentration of stem cells per unit volume of aspiration. Human and animal study data (George F. Muschler et al. JBJS 79:1699-1709, 1997) suggests that for the highest stem cell concentration results, the aspiration volume should not exceed 2 ccs for every centimeter of linear travel of the needle. Using a manual process to control the collected volume and location of the needle results in a procedure that is very technique dependent and yields inconsistent results.

In order to extract an adequate sample, doctors may insert the needle into several different parts of the iliac crest. In some cases this requires a multitude of insertions (e.g., six or even more for leukemia patients). The above described methods can be extremely painful for a patient and in some cases deters individuals from donating bone marrow and deters patients from undergoing a necessary bone marrow test.

Accordingly, a need exist for a bone marrow aspirator and method thereof that increases the efficiency in obtaining bone marrow from a patient. Thereby minimizing patient discomfort.

BRIEF SUMMARY OF THE INVENTION

Disclosed herein is a bone marrow aspirator including a housing, a pump mounted on the housing, a reservoir connected to a first part of the pump, and a needle connected to a second part of the pump. The needle is further coupled to a screw element that moves the needle along a longitudinal axis of the screw when the screw is rotated. The screw element that moves the needle further includes a driven gear. The pump is connected to an input shaft having a drive gear mounted at a first end and a rotary input element at a second end. The drive gear is selectively engageable with the driven gear by movement of the input shaft from at least one of a first position and second position to a third position. In the first and second positions the drive and driven gear are not engaged so there is no needle movement. In the third position the drive and driven gear are engaged. In the first position the heparin is applied to coat the flow passageways of the device. In the second position the device is primed and in the third position the bone marrow is aspirated.

Further, in the first position anticoagulant can be aspirated through the needle. In the second position bone marrow can be aspirated without moving the needle. This is used to prime the pump. In the third position, the needle is withdrawn while the bone marrow is aspirated into the reservoir. Further, in the third position, the needle can be displaced proportionally to displacement of the volume in the reservoir. The proportional displacement can be determined by the gearing ratio of the drive gear to the input gear.

In the first position in which the heparin is applied, the drive gear is disengaged and the rotary input element can only rotate in a first direction. In the second position the drive gear is disengaged and the rotary input element can only rotate in a second direction. This is used to prime the system. In the third or aspiration position the drive gear is engaged and the rotary input element can rotate in at least one of a first direction and a second direction. When engaged to the screw, the pump only operates in one direction—suction. This is done as a safety means to ensure that air is not pumped into the patient. This is achieved with a one way clutch.

The bone marrow aspirator can also include, a sleeve housing the needle and an indicator for determining displacement of the needle. The indicator displaces in relation to the rotation of the screw element. Further, the pump can be a peristaltic pump.

Also, disclosed herein is a method for using the above described bone aspirator. The reservoir needs to be pre-filled with anticoagulant or the device can be set in the second position and the anticoagulant can be aspirated into the reservoir and thereby flush the circuit. In use, the aspirator is provided to a user, the user selects the third position and displaces the needle from the sleeve a desired puncture depth; and the selector switch is then placed in a first position and the rotary input element is rotated in a first direction to flush the fluid path from the reservoir through the pump and through the needle with an anti-coagulant. This is done prior to inserting the needle into the patient. The switch is then placed in the second position to prevent dispensing any material into the patient. The needle is then delivered into bone until the sleeve hits cortical bone. With the needle in the bone, the selector switch is placed in the second position and the pump rotated in a second direction via the handle to start the aspiration of bone marrow. The selector switch is then placed in a third position. In the third position, the pump is rotated in the second direction to retract the needle and simultaneously actuate the pump.

It should be noted that features and methods and functionalities of the present invention, including but are not limited to features and methods and functionalities for engaging one tool (or parts thereof) with one or more other tools (or parts thereof) or with the implants (or parts thereof), and vice-versa; for addressing, avoiding, manipulating, or engaging the patient's anatomy; for aligning one or more tools with anatomic or non-anatomic reference points; and for aligning the tools and implants with one another and/or a treatment space; are not and should not be limited to those embodied in and achieved by the structures and methods of the specific embodiments described and shown, but rather the structures and methods of the specific embodiments described and shown are merely examples of structures and methods that can achieve certain features and methods and functionalities of the present invention. In certain embodiments of the present invention, a user (e.g., doctor, nurse, etc.) is provided a bone marrow aspirator for extracting samples of bone marrow from a patient. The bone marrow aspirator includes a housing having a pump and a reservoir attached to the housing. Further, extending from the housing is a sleeve containing a needle. This needle connects to a tube running through the pump connecting to the reservoir. Thus, by actuating the pump material (e.g., anticoagulant, bone marrow, etc.) can be pumped between the reservoir and the needle.

Further, in certain embodiments of the present invention, the needle can displace toward and away from the sleeve. The needle is displaced by engaging (e.g., rotating) a rotary input element. This same rotary input element also actuates the pump. In order to control the direction of flow between the needle and the reservoir, the rotational direction of the rotary input device, and needle displacement—a selector switch gives a user the option of three possible positions. In the first position, the rotary input device can rotate in both a first and second direction and material (e.g., anticoagulant) can aspirate from the reservoir to the needle. Note this is done prior to placing the needle in the patient. Further, in the first position the needle cannot be displaced. In the second position, the rotary input device can only rotate in a second direction and material (e.g., bone marrow) can only aspirate from the needle to the reservoir. Similar to the first position, in the second position the needle cannot be displaced. In the third position, material can be pumped between the needle and the reservoir and the needle can be displaced toward the sleeve upon rotation of the rotary input element or handle in the only allowed direction. Further, in the third position, the needle displacement is proportional to the volume displacement in the reservoir.

In certain embodiments of the present invention, when the bone marrow aspirator is provided to a user, the selector switch is placed in the third position. In the third position the user can rotate the rotary input element in a first direction causing the needle to displace away from the sleeve or rotate the rotary input element in the second direction causing the needle to displace toward the sleeve. After displacing the needle the desired amount, the user places the selector switch in the first position. In this position, the user rotates the rotary input element in the first direction pumping anticoagulant, located in the reservoir, out of the needle. After pumping the anticoagulant, the needle and sleeve are inserted into a patient until a desired depth is reached (e.g., the sleeve touches the cortical tissue of the patient). Rotation of the handle in the second direction aspirates bone marrow from the patient through the needle into the reservoir. Prior to filling the reservoir with bone marrow rotation of the handle in the second direction primes the pump, filling the fluid path circuit with bone marrow prior to starting needle movement. The priming is stopped before the bone marrow reaches the reservoir. After priming, the user places the selector switch in the third position and rotates the rotary input element in the second direction causing the needle to displace into the sleeve while simultaneously actuating the pump.

These and other embodiments of the present invention will be described in more detail below.

BRIEF DESCRIPTION OF THE DRAWINGS

These and other aspects of this invention are explained and elaborated through reference to the embodiments described as examples below. Examples of embodiments are described in the following with reference to the following drawings.

FIG. 3 is an isometric view of the aspirator of FIG. 1 with the cover removed showing the displacement mechanisms of the needle;

FIG. 3A is an enlarged view of the shuttle of FIG. 3;

FIG. 9A shows the bone marrow aspirator with the selector switch in a position in which an anti-coagulant may be pumped from the reservoir through the needle;

FIG. 11A is a front view of the bone marrow aspirator with the pump selector switch in the middle position in which the needle is retracted with the pump activated;

DETAILED DESCRIPTION

Figure 1:
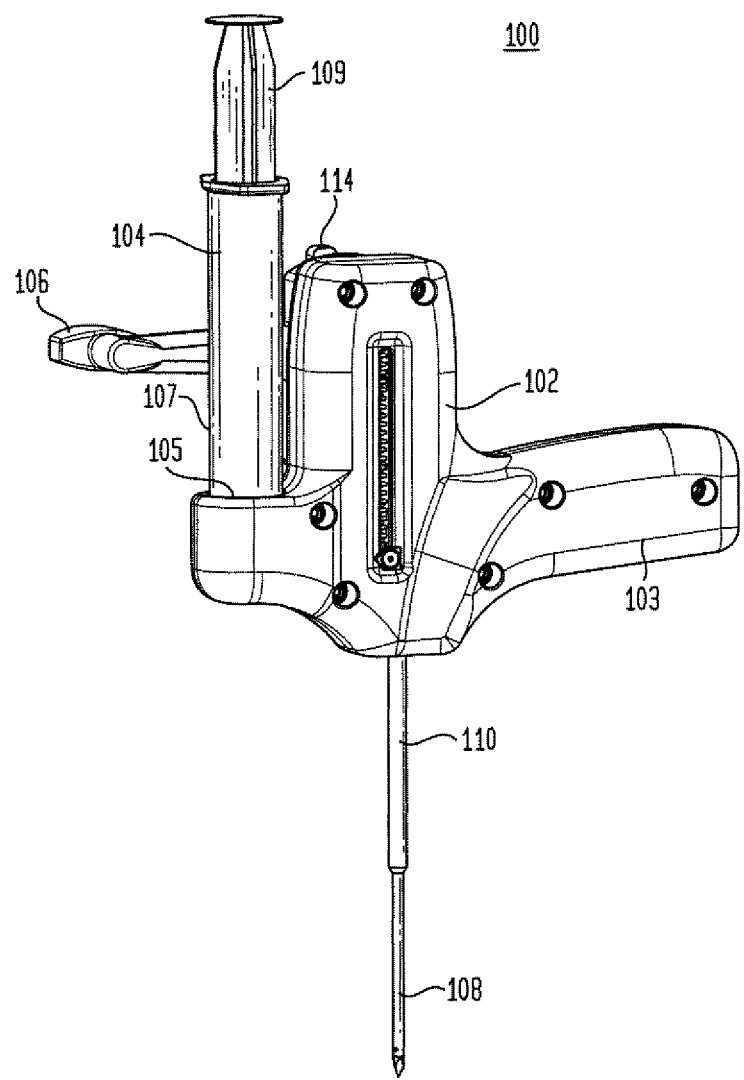
FIGS. 1-2 are isometric views from opposite sides of a bone marrow aspirator in accordance with certain embodiments of the present invention.
Figure 2:
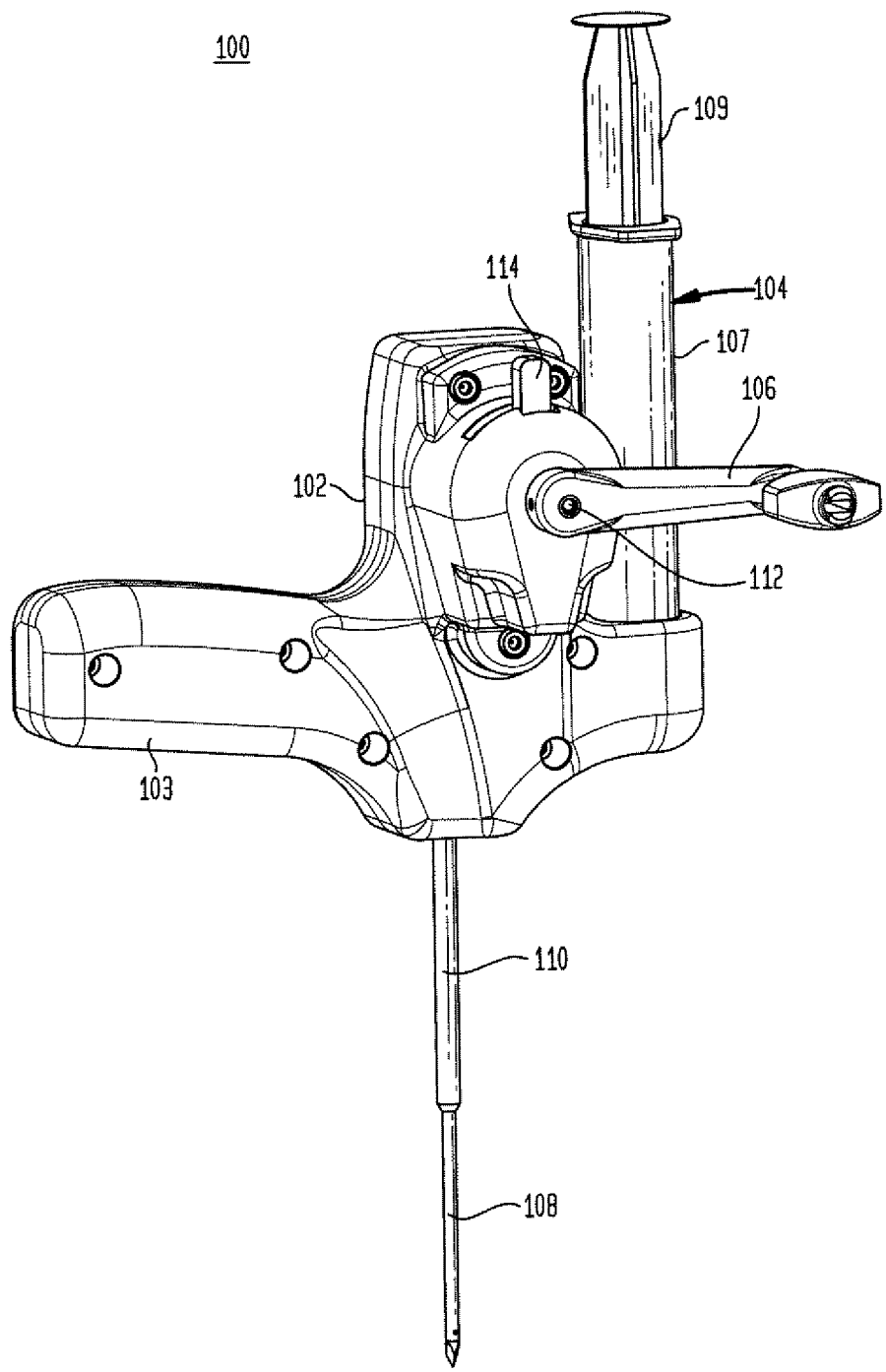

Referring to FIGS. 1-2, there is shown an isometric view of the bone marrow aspirator of the present invention generally denoted as 100. Bone marrow aspirator 100 includes a housing 102 with a pump (see FIG. 4) mounted on the housing. In the preferred embodiment a handle 103 is formed on one end of housing 102. Also in the preferred embodiment a reservoir 104 is mounted on a receptacle 105 on housing 102. Reservoir 104 can be a syringe having an outer barrel 107 that threads into receptacle 105 on housing 102. A plunger 109 is received within barrel 107 and seals an open end of the barrel. The threading of the barrel 107 in receptacle can, for example, be a sealing pipe thread. Any method for mating reservoir 104 with housing 102 deemed suitable can be used. Further, a rotary input element, such as hand crank 106, can be rotated by a user thereby actuating the pump and causing material to be pumped between a needle 108 and reservoir 104 as well as displace (i.e., advance or retract) needle 108 from a sleeve 110 which acts to guide needle 108. As will be discussed in greater detail below reservoir 104 is connected to needle 108 by a tube system 308 through which a pump 400 can selectively pump fluid, such as an anticoagulant, from reservoir 104 to needle 108 and vice-versa.

Figure 4:
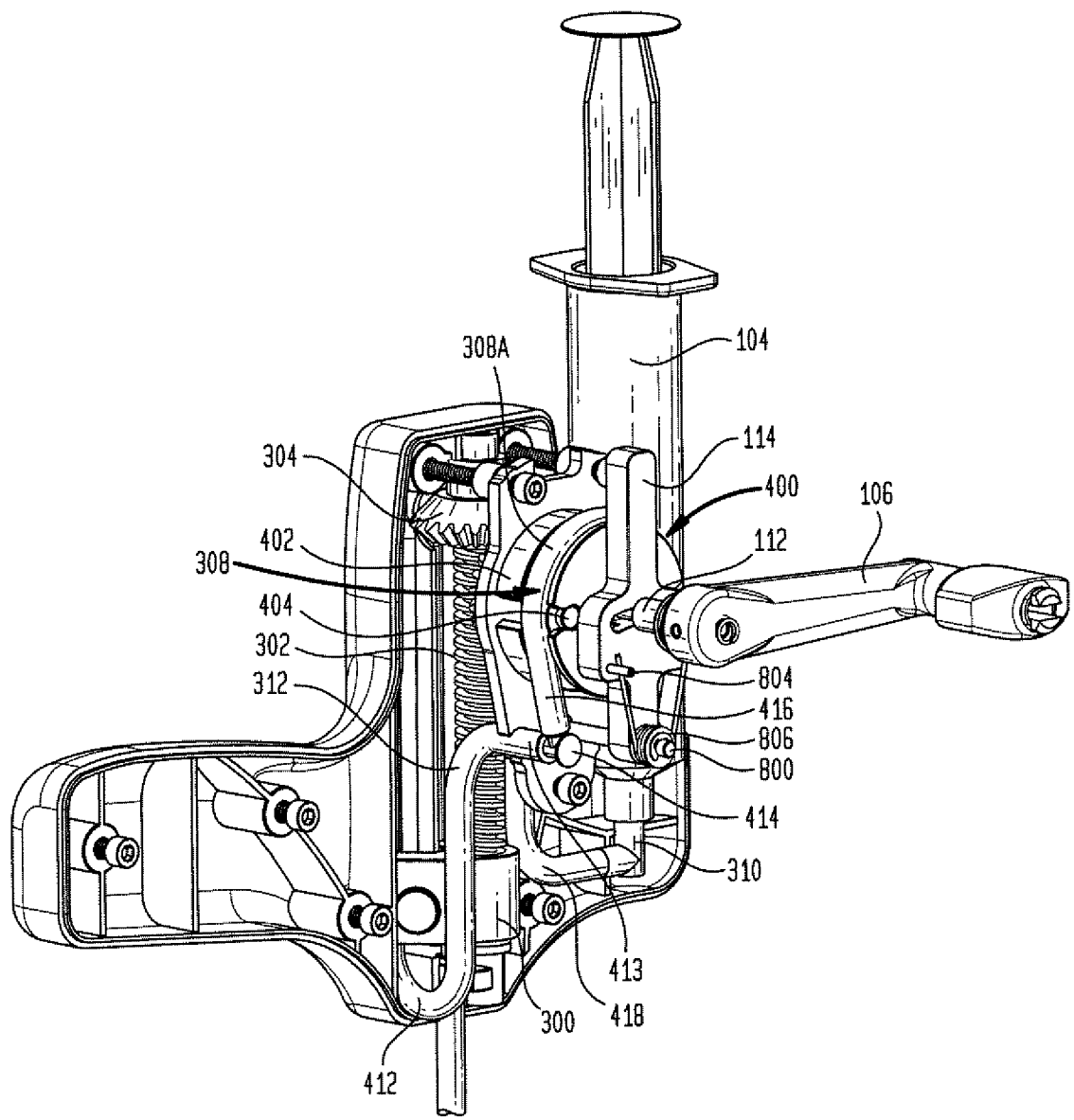
FIG. 4 is an isometric view of the aspirator of FIG. 2 with the cover removed showing a pump mechanism mounted on the housing of the bone marrow aspirator.

Referring to FIG. 4 a selector switch 114 controls the direction of flow between the needle and the reservoir, the rotational direction of rotary input device 106, and the ability to displace needle 108.

In the preferred embodiment, rotary input element such as handle 106 is a hand crank attached to input shaft 112. In the preferred embodiment shaft 112 drives a reversible pump as well as an extension-retraction system for needle 108. If rotary input element 106 is a hand crank the user actuates the pump by rotating crank 106. Alternatively, rotary input element 106 can be a motor attached to input shaft 112. If rotary input element 106 is a motor the user actuates the pump via a controller which at a minimum is an on-off switch. It will be apparent that any reasonable actuator can power the pump and/or needle extension and retraction system.

Referring to FIGS. 3 and 4, needle 108 can be displaced by rotating rotary input element 106. This displacement occurs because needle 108 is mounted on a shuttle 300 having a threaded bore 301 threadably connected to a threaded shaft 302. Needle 108 is fixedly mounted on shuttle 300 and is in communication with a slot 303 therein. Needle 108 has a hook shaped end 305 that is captured in slot 303 by a pin or screw with end 305 of the needle end connected to an end of a tube 412 which tube runs from the pump 400 at an end 413 thereof. Shaft 302 is driven by beveled drive gear 304 which in turn is driven by input gear 306 which is mounted on drive shaft 112. As threaded shaft 302 rotates, shuttle 300 moves up and down along shaft 302 depending on the direction of rotation of crank 106. Because needle 108 is fixedly attached to shuttle 300, as shuttle 300 moves needle 108 moves with it. Further, bevel gear 304 can selectively engage input gear 306 so that the pump can be driven by crank 106 without the needle drive system being operated. Drive gear 304 and input gear 306 can be miter gears that mesh together. Input gear 306 is attached to rotary input handle 106 by input shaft 112. Thus, rotating rotary input element 106 causes input gear 306 to rotate whether connected to beveled drive gear 304 or disengaged therefrom. If input gear 306 engages drive gear 304 then rotating rotary input element 106 causes needle 108 to move with respect to sleeve 110.

A selector switch 114 is mounted on shaft 112 which allows the drive system for needle 108 to be selectively engaged and to selectively drive a pump 400. Selector switch 114 has three possible positions for controlling engagement of drive gear 304 with input gear 306. Also, in certain embodiments of the present invention, selector switch 114 can limit the direction of rotation of rotary input element 106. For example, in a first position drive gear 304 does not engage input gear 306 and rotary input element 106 can only rotate in a first direction. Thus, rotating rotary input element 106 in the first position injects material (e.g., anticoagulant) from reservoir 104 through needle 108. In the second position, drive gear 304 remains disengaged from input gear 306, however, rotary input element 106 can only rotate in a second direction. Thus, rotating rotary input element 106, in the second position, aspirates material (e.g., bone marrow) from needle 108 to reservoir 104. In the third position, drive gear 304 engages input gear 306 and rotary input element 106 can rotate in both the first and second directions. Thus, rotating rotary input element 106, in the third position, aspirates material between needle 108 and reservoir 104 and simultaneously displaces needle 108 toward and away from housing 102 depending upon the direction of rotation of rotary input element 106 and consequently shaft 112.

Further, in the third position, as needle 108 is displaced the volume of aspirate drawn into reservoir 104 is proportional to the linear displacement of the needle 108. That is, as needle 108 retracts into sleeve 110 material (e.g., bone marrow) is pumped into reservoir 104 thereby filling reservoir 104 in an amount proportional to the displacement of needle 108 toward housing 102. This proportionality is controlled by the gear ratio between drive gear 304 and input gear 306. It can also be controlled by a change in pump tubing ID and/or a change in pump diameter.

Referring to FIGS. 3 and 4 reservoir 104 connects to plastic tube portion 418 at an end 310 thereof. Tube system 308 continues to pump 400 with a portion 308A extending around the pump. A second tube portion 312 leaves pump 400 and has an end 412 that connects with bore 303 in shuttle 300 which bore is connected to end 305 of needle 108. Thus, with the selector 114 in the center position rotating rotary input element 106 actuates the pump thereby pumping material between reservoir 104 and needle 108.

In the preferred embodiment of the present invention, rotation of handle 106 in either the first or second direction can be limited by a one way clutch. For example, with the selector in the first position, rotation in either direction is allowed because a one way clutch allows rotation in either direction by overcoming the slip clutch. This allows the anticoagulant to be pumped from the reservoir. It will be apparent that any reasonable restriction on rotation can be used to limit movement in a direction.

Referring to FIG. 4, pump 400 is shown as a peristaltic pump. Pump 400 can include pump housing 402 and a pump roller 404. Pump housing 402 can provide a trough or groove for portion 308A of tube system 308 to sit in. As a user rotates rotary input handle 106, shaft 112 rotates, causing pump housing 402 to rotate causing pump roller 404 to substantially compresses tube portion 308A.

Further, tube system 308 can include several separate sections to facilitate its fit within housing 102. For example, tube 308 can include a first tube section 312 with an end 412 connected to the needle end 305 and a second end 413 connected to a first connector 414. Connector 414 is a plastic connector with two internal bores at right angles. Tube section 308A is attached to the other end of connector 414 and runs around the groove in pump 400 which in turn is connected to section 308 via a similar second connector (not shown). Finally a third tube section 418 connects from the second connector (not shown) to reservoir 104. Multiple tube sections may be advantageous because, for example, the tube used in the pump may require different material properties for handling the stress of being repeatedly compressed during pumping.

In the preferred embodiment, pump 400 is a hand cranked peristaltic pump. A hand crank peristaltic pump can provide additional user control because as the user rotates rotary input handle 106 the pump is actuated. Alternatively, pump 400 can be a motorized peristaltic pump. For example, rotary input element 106 can be a motor connected to input shaft 112. Thus, supplying power to the motor would cause input shaft 112 to rotate thereby actuating pump 400. Although pump 400 is described as a peristaltic pump any other pump deemed suitable can be used.

Figure 5:
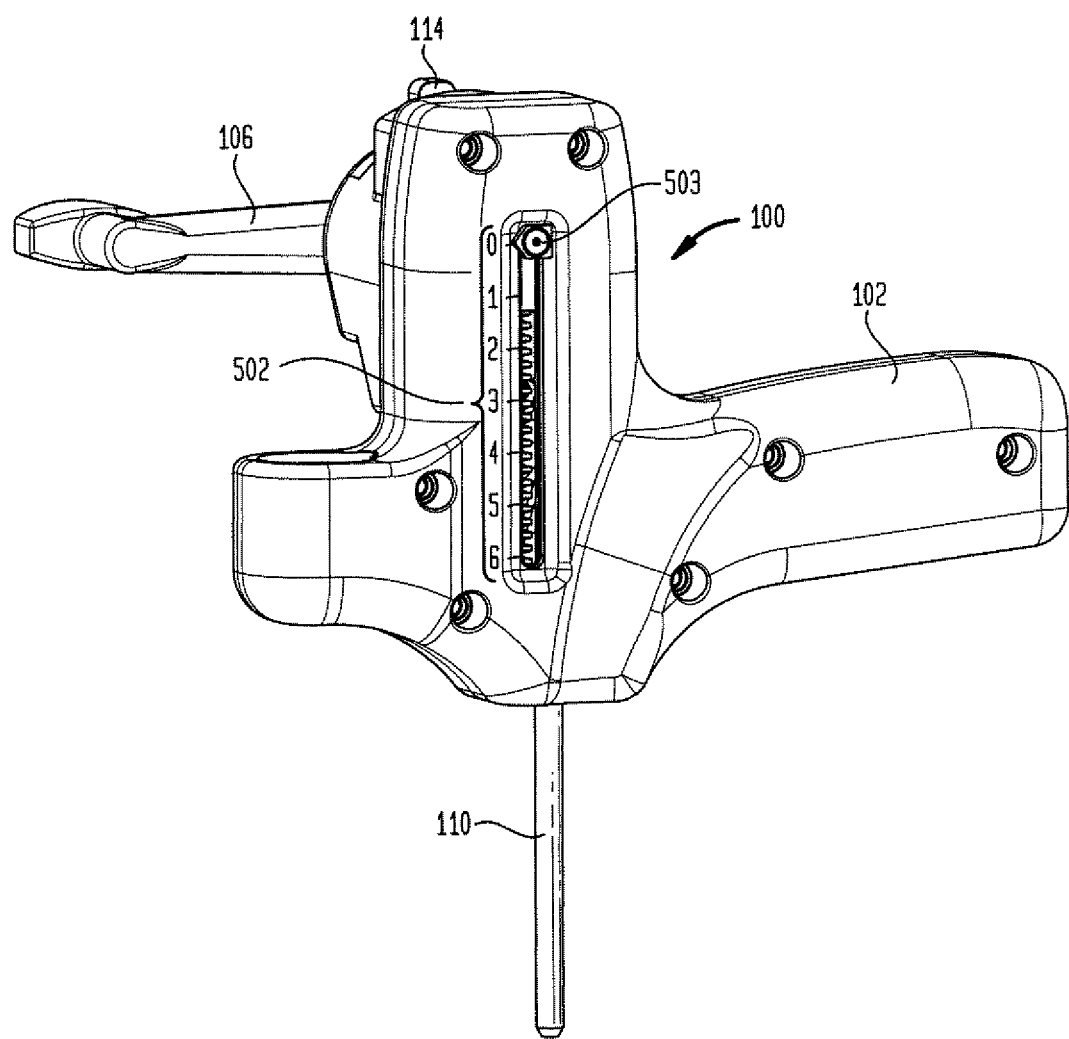
FIG. 5 is an isometric view of the bone marrow aspirator of FIG. 1 housing with the needle fully retracted.

Referring to FIG. 5 bone marrow aspirator 100 has needle 108 positioned within housing 102 substantially surrounded by rigid sleeve 110. To accomplish this selector switch 114 is placed in the third position so the needle can be displaced by rotating rotary input element 106 in a first/second direction. In the preferred embodiment of the present invention a scale 502 is located on the side of housing 102. Scale 502 has a pointer 503 which indicates the location of element 300 within housing 102 and thus the location of the needle (not shown). Preferably the scale is in centimeters. As shown in FIG. 5, the needle is fully retracted within the housing 102 and sleeve 110. Thus, the pointer indicates the needle position is at zero.

Figure 6:
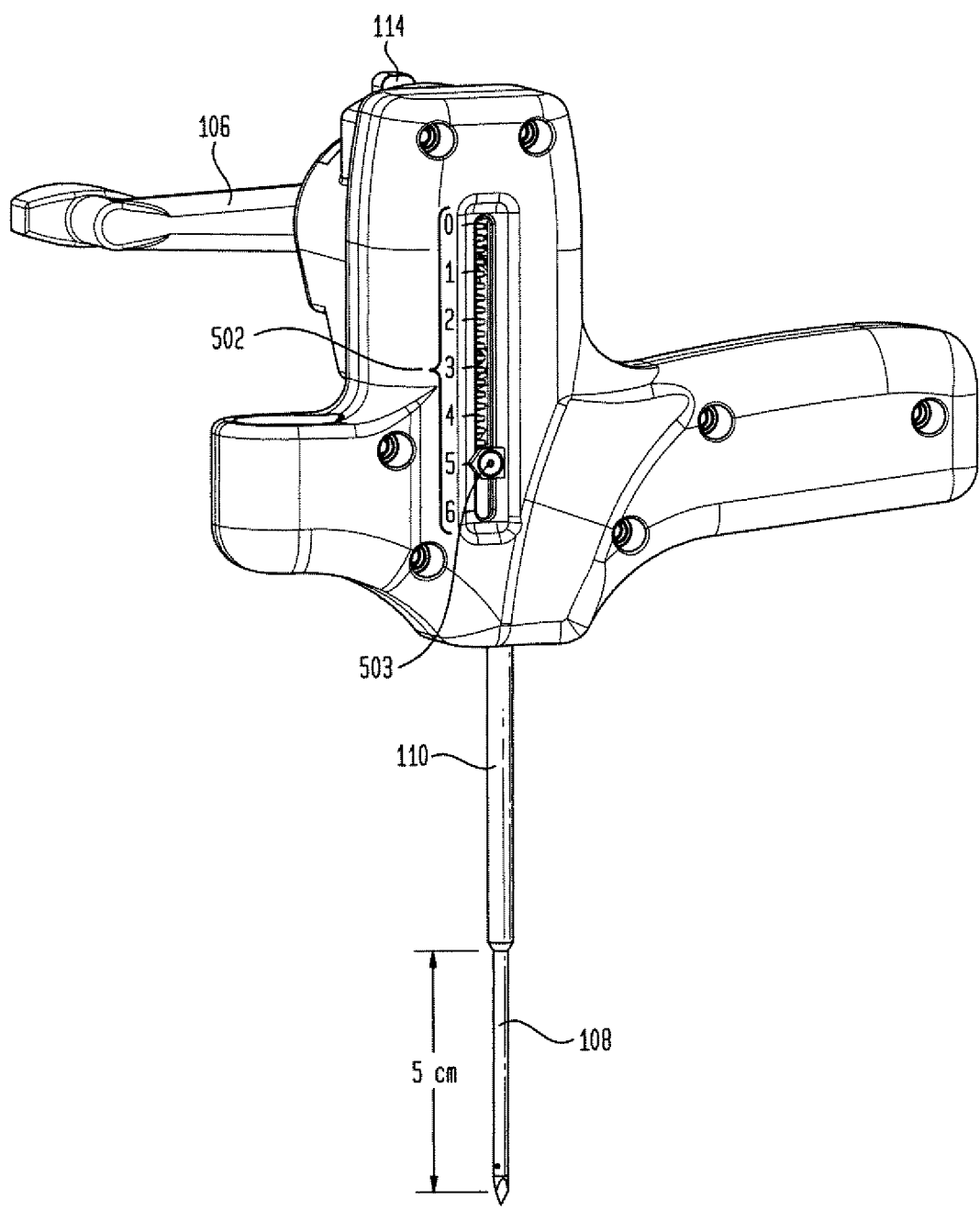
FIG. 6 is an isometric view of the bone marrow aspirator of FIG. 5 with the needle extended.

Referring to FIG. 6, with selector switch 114 in the third position, the user rotates rotary input element 106 in a direction causing element 300 and needle 108 to move downwardly and out of sleeve 110. As shown, for example, pointer 503 of scale 502 indicates that needle 108 has been displaced from sleeve 110 approximately five centimeters. Needle 108 can be moved a maximum distance depending on the size of housing 102 and, as shown in FIG. 6, has a maximum displacement of 6 centimeters.

Figure 7:
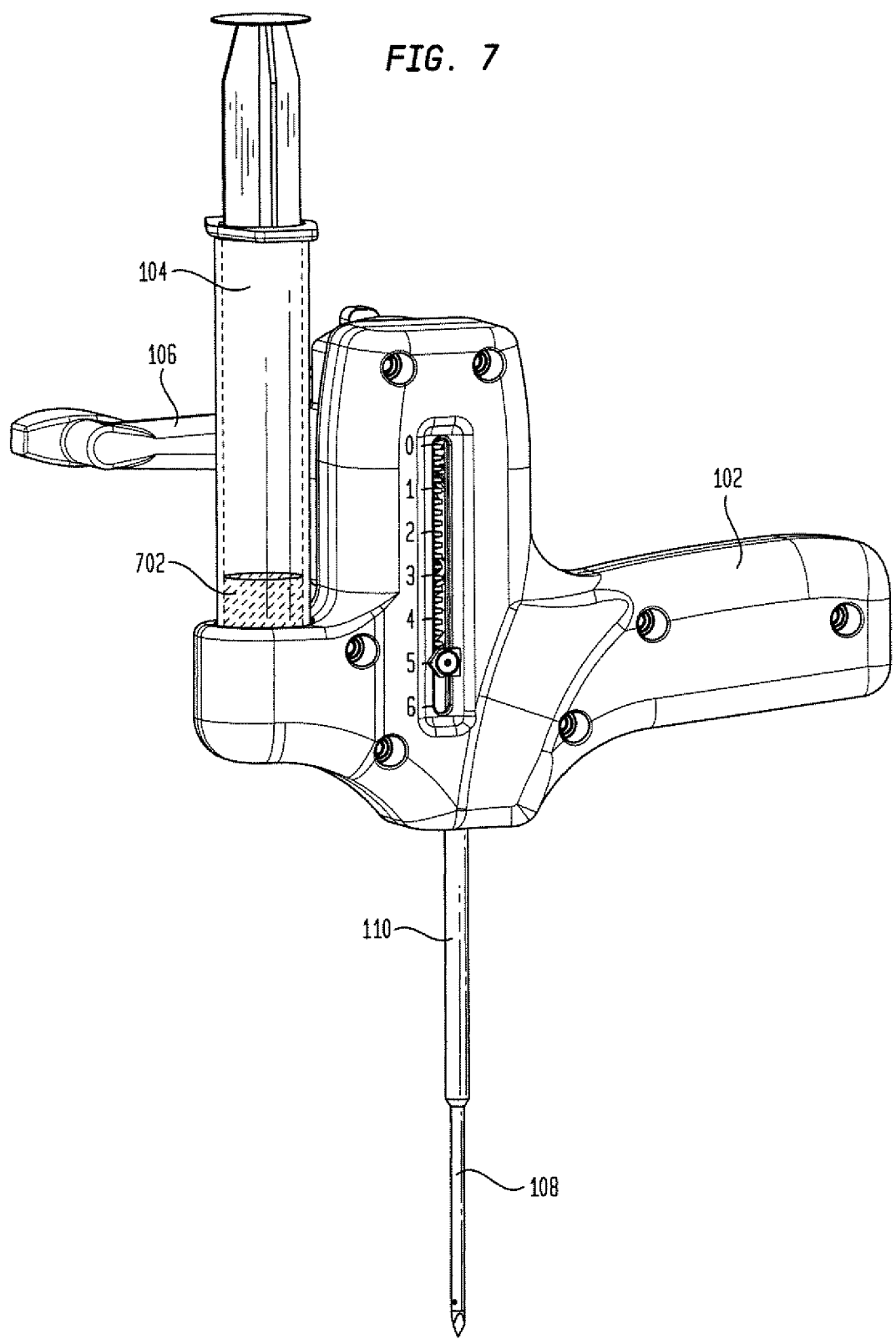
FIG. 7 is an isometric view of the bone marrow aspirator of FIG. 1 with a reservoir containing an anticoagulant.

Referring to FIG. 7, with selector switch 114 in the center or third position, material can be aspirated and pumped between needle 108 and reservoir 104 via a tube system 308 by pump 400 by turning handle 106 counter clockwise in FIGS. 3, 6 and 7 (clockwise in FIG. 4). Note in the third position the handle can only turn in this direction. Further, as discussed above, reservoir 104 can initially include a material 702, such as an anticoagulant, to be pumped to needle 108 prior to it being placed on bone. In this operation the selector switch 114 is moved to a second position shown in FIG. 9B in which the gears 304 and 306 are no longer engaged but the pump is operated. Turning the handle clockwise in FIGS. 6 and 7 moves fluid from reservoir 104 and out needle 108. Material 702 can include any anticoagulant, such as, but not limited to, Heparin, Warfarin, Acenocoumarol, Phenprocoumon, or any other anticoagulant deemed suitable. For example, rotating rotary input handle 106 clockwise will pump Heparin from reservoir 104 to needle 108.

Figure 8A:
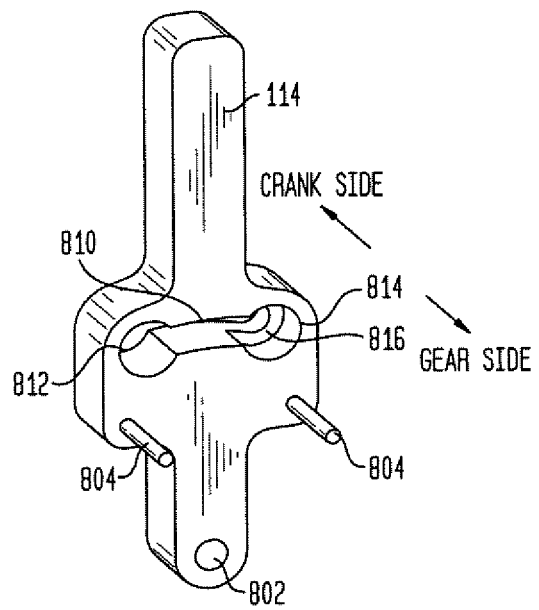
FIG. 8A is an isometric view of the pump selector switch of the bone marrow aspirator of the present invention.
Figure 8B:
FIG. 8B is a side view of the selector switch of FIG. 8A.
Figure 8C:
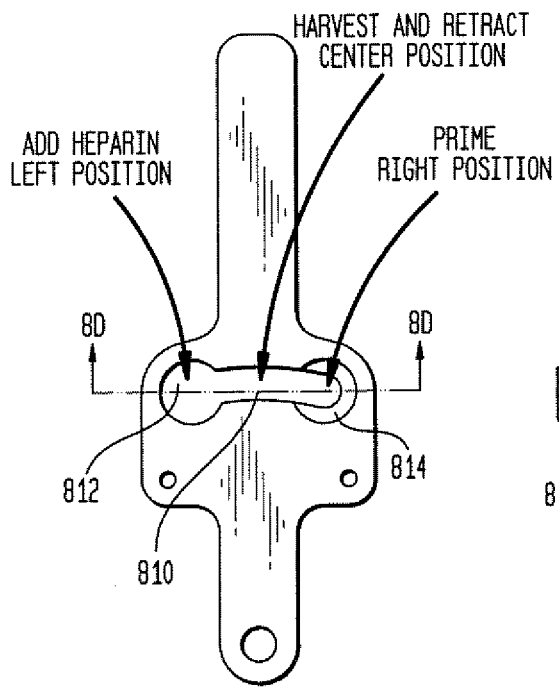
FIG. 8C is a front view of the pump selector switch of FIG. 8A.
Figure 8D:
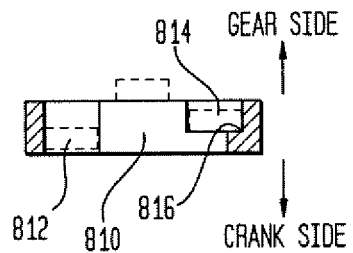
FIG. 8D is a cross-sectional view of the selector switch along lines 8D-8D of FIG. 8C.

Referring to FIGS. 8A through 8D there is shown a selector switch 114 of the present invention. Selector switch 114 is rotatably mounted within housing 102 by a pivot pin 800 which is received within bore 802 at the bottom end of the selector switch 114. A pair of pins 804 is provided to engage ends of a coil spring 806 which tends to return the switch 114 to its third position which is centered between the first and second positions. As can be seen in FIGS. 8A and 8D the crank includes a slot 810, a bore 812 having a constant diameter and a bore 814 having a step 816 of a smaller diameter.

Figure 9B:
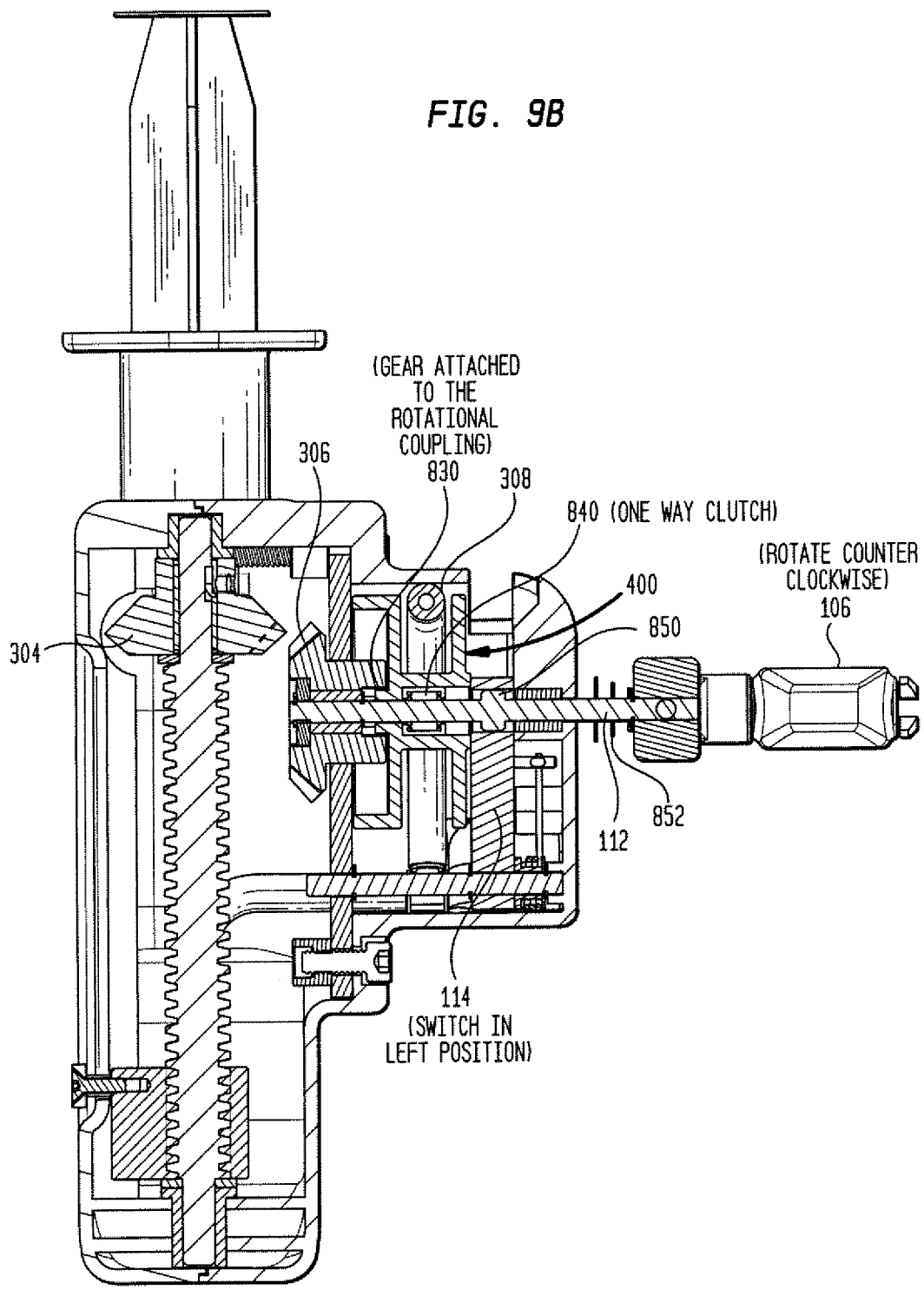
FIG. 9B is a cross-sectional view of the bone marrow aspirator of FIG. 9A along lines 9B-9B.
Figure 10A:
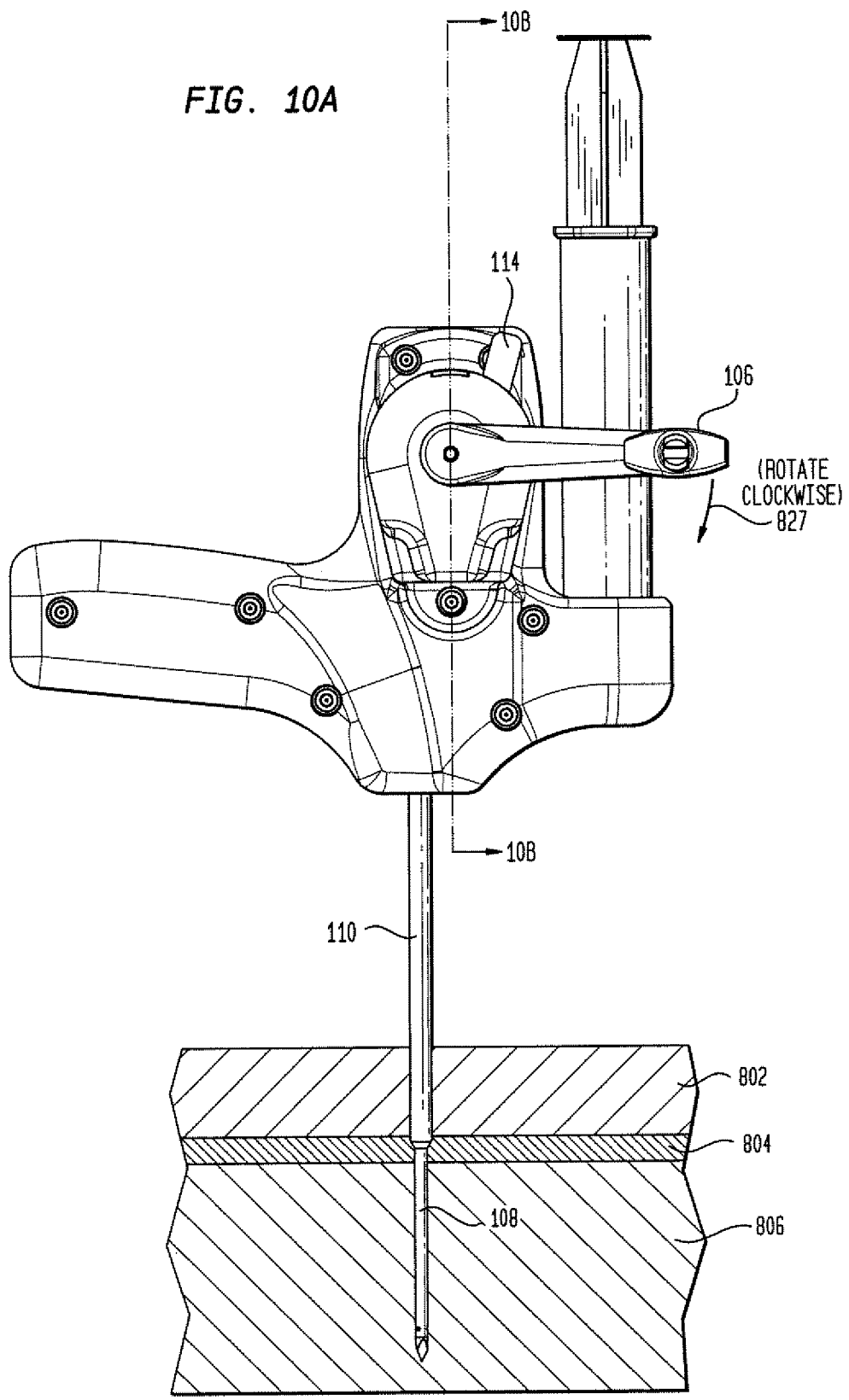
FIG. 10A is a front view showing the pump selector switch in a second position in which the needle and bone marrow are withdrawn from the bone canal.
Figure 10B:
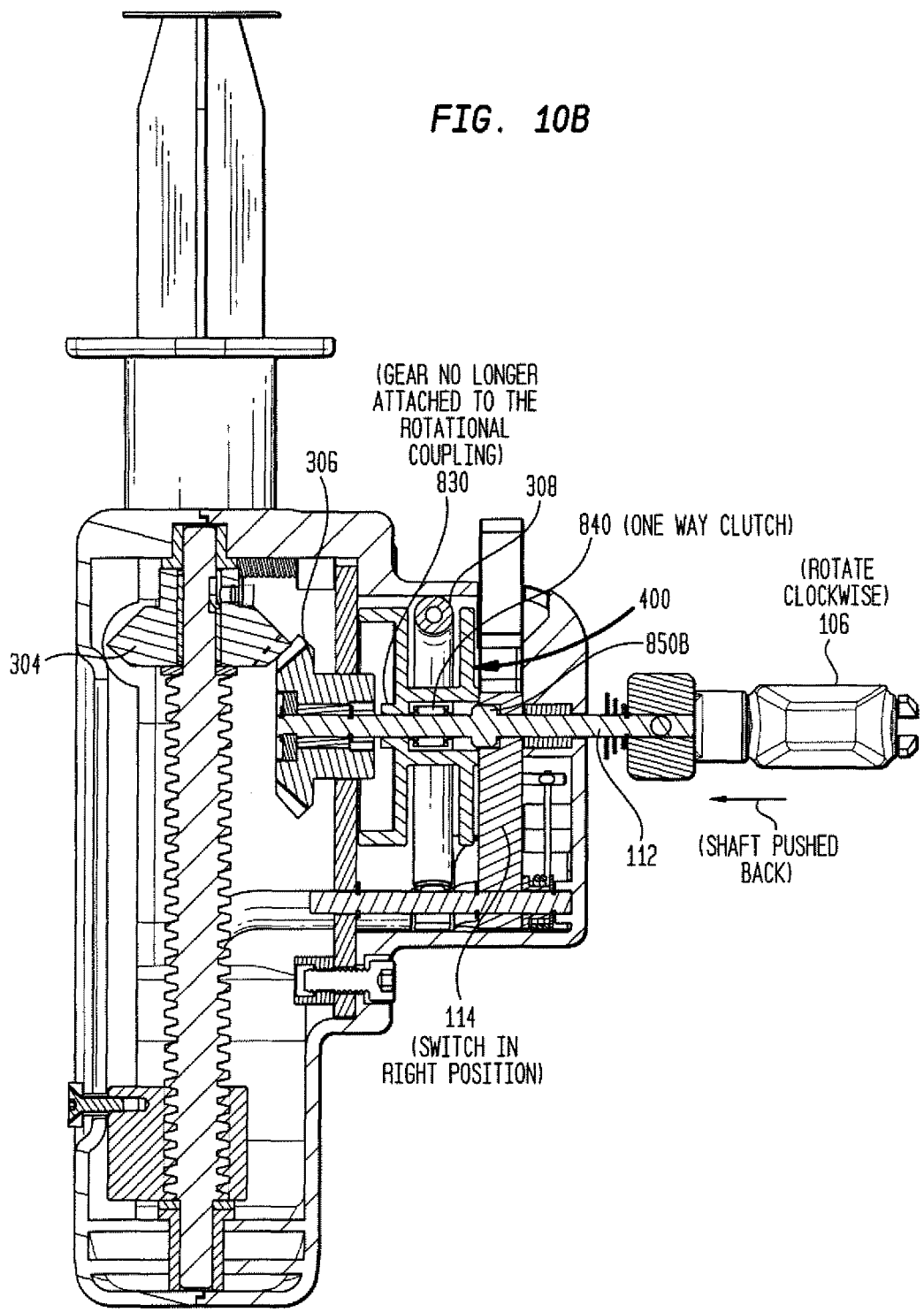
FIG. 10B is a cross-sectional view of the bone marrow aspirator of FIG. 10A along lines 10B-10B.
Figure 11B:
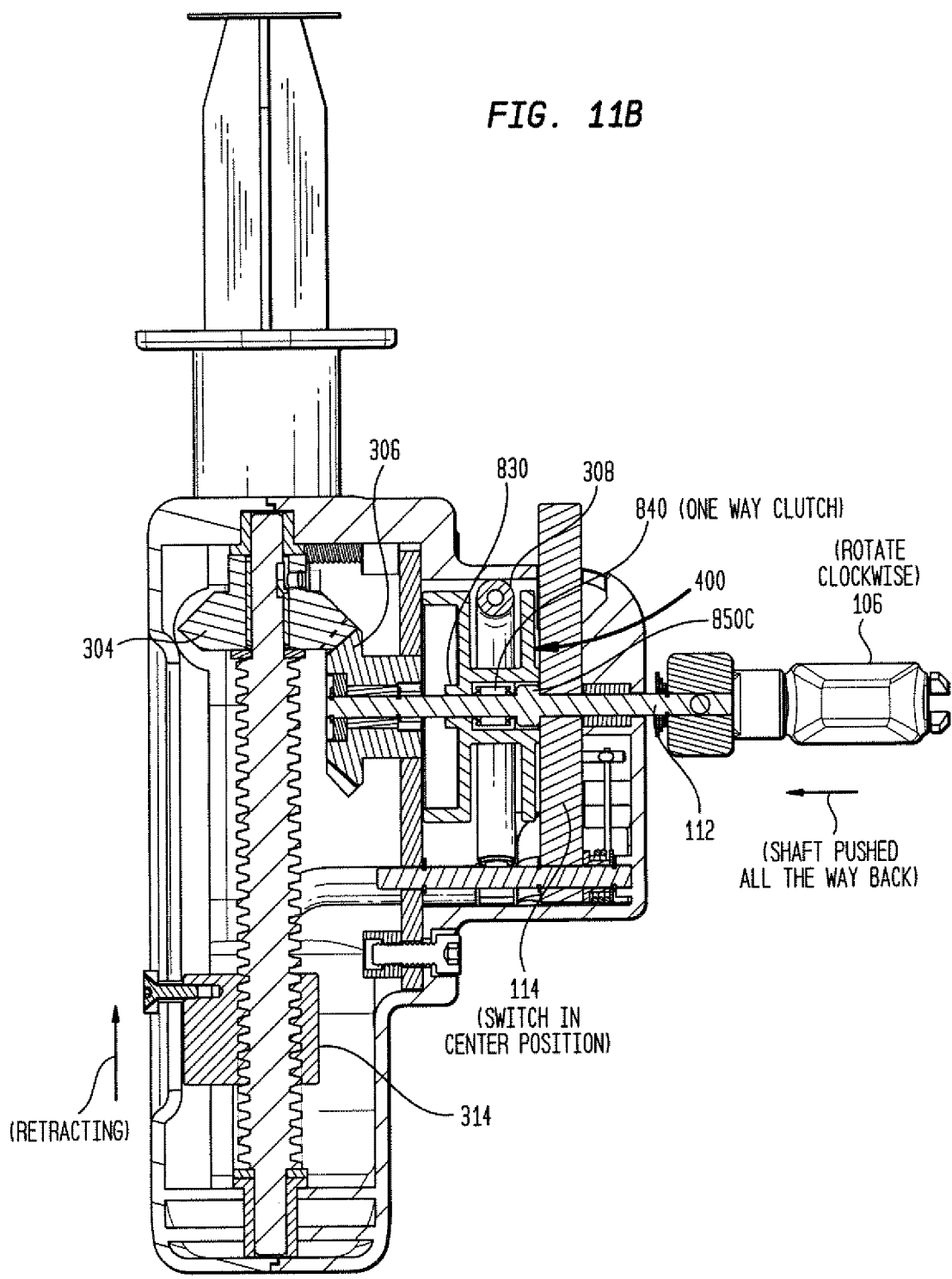
FIG. 11B is a cross-sectional view of the bone marrow aspirator of FIG. 11A along lines 11B-11B.

As can be seen in FIGS. 9B, 10B and 11B, shaft 112 includes a stop element 850 which is located on the side of switch 114 opposite the handle 106 and adjacent the drive gear 306. The spring 52 is located between the housing 102 and the handle 106 to bias the shaft 112 and therefore gear 306 mounted at an end thereof out of engagement with gear 304. Thus, when stop element 850 is aligned with bore 812 of switch 114 when the selector switch is in the first position the stop 850 extends through bore 812 and gear 306 is disengaged from gear 304. However, in this position rotation of handle 106 in the first direction will operate pump 400 moving fluid from reservoir 104 to needle 108. Note in the first position the handle may be rotated in either direction. In the preferred embodiment one would pre-fill the reservoir with a desired amount of anticoagulant—enough to coat fluid path and enough for volume of bone marrow to be captured. Both volumes would be specified in the instructions for use. The user would connect the pre-filled reservoir, flush the fluid path, and then apply the device to the patient.

When selector switch 114 is moved to the opposite end of slot 810 stop element 850 of shaft 112 engages step 816 of bore 814 as shown in FIG. 10B. In this position, the gears remain disengaged and the handle 106 may be turned in the opposite direction to move fluid by aspiration through the needle 108 to the reservoir 104. Once the pump 400 is primed by rotation in this direction, the selector switch 114 is moved into the middle or third position which causes gears 304 and 306 to engage and the needle 108 to be withdrawn from the bone marrow area of the bone while simultaneously aspirating bone marrow through tubing system 308 by the action of pump 400. This is accomplished by pushing the shaft in and the springs move the selector switch to the middle position.

Referring to FIGS. 9A and 9B, the needle 108 is inserted into the patient to a desired depth. For example, needle 108 and sleeve 110 can pass through soft tissue 802 of the patient until sleeve 110 contacts cortical bone 804. With sleeve 110 contacting cortical bone 804 needle 108 is forced through the cortical bone and into the cancellous bone 806 of the patient.

After needle 108 is inserted into the desired position, selector switch 114 is placed in the second (left) position. In the second position, the drive gear remains disengaged and thus the needle can not move. Further, in the second position a one way clutch 840 prevents rotation of the pump in one direction and allows rotation in only one direction (counter clockwise in FIGS. 4 and 9A) to move aspirate from the needle to the reservoir. rotary input element 106 can only move in a second direction.

Referring to FIGS. 11A and 11B, selector switch 114 is placed in the third position which is in the center in FIG. 11A. Thus, the drive gear 304 is engaged with the input gear 306, and needle 108 can be moved toward or away from housing 102 within sleeve 110. Further, material can be aspirated from needle 108 and pumped to reservoir 104 via tubing system 308 and pump 400. As a user rotates rotary input handle 106 in the clockwise direction in FIG. 11A the needle 108 moves into housing 102 as aspirate is pumped into reservoir 104. For example, scale 502 displays how far needle 108 has retracted. As needle 108 retracts into housing 102 through sleeve 110 reservoir 104 fills with a proportional volume of bone marrow aspirate. Needle 108 continues to be retracted until fully within housing 104 (pointer 503 at 0 cm) and the system 100 is then removed from the patient.

Further, although described as having three positions the selector switch described can include any number of positions. For example, the first and second positions can be combined wherein in this new first position drive gear 304 is not engaged with input gear 306, however, rotary input element 106 can rotate in both the first and second direction. Even further, the third position could be divided into two new positions: a new third and a fourth position. In the new third position and the fourth position, drive gear 304 is engaged with input gear 306. However, in this new third position rotary input element 106 can only move in one direction while in the fourth position rotary input element 106 could move in the opposite direction.

Figure 12:
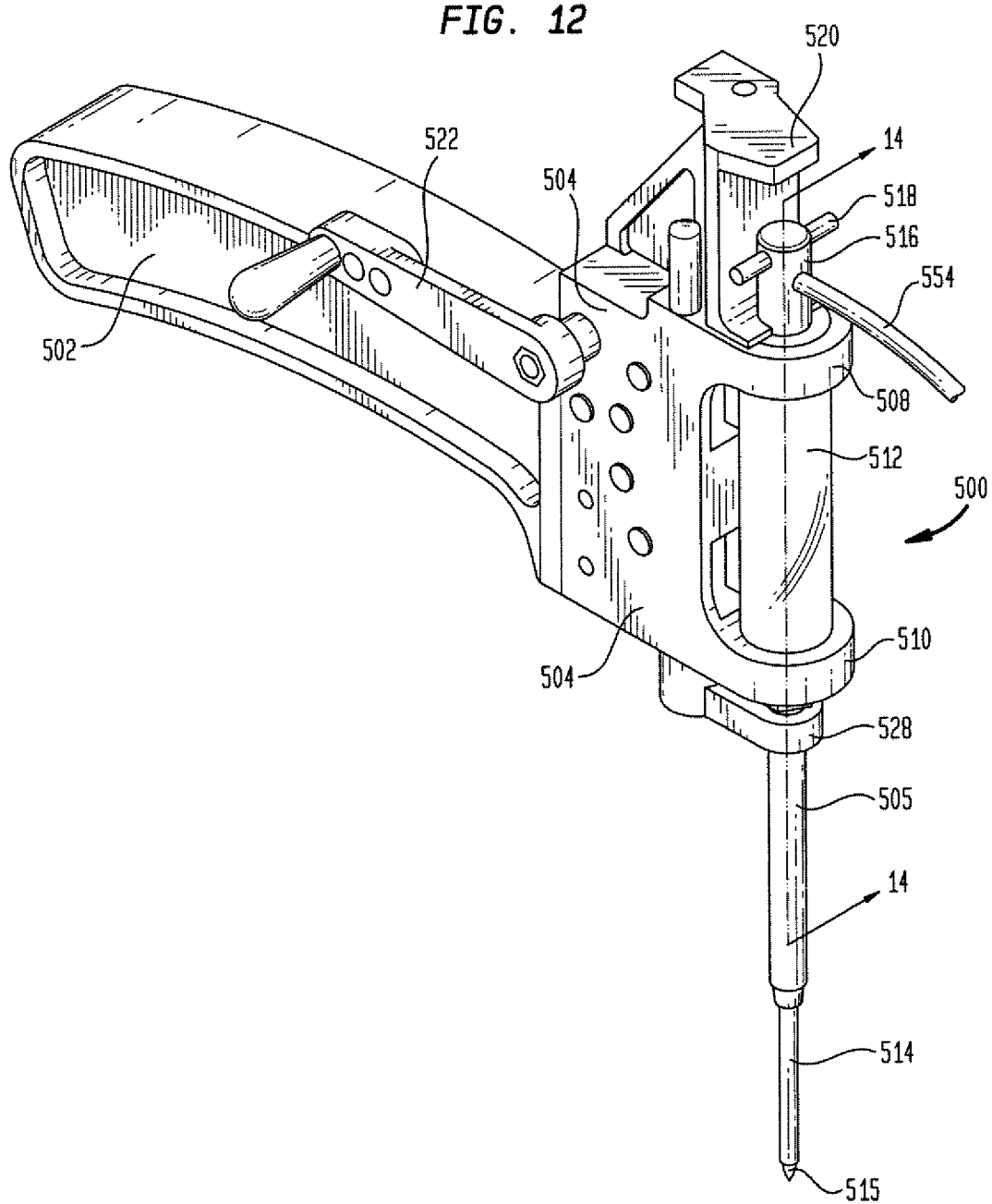
FIG. 12 is a perspective view of an alternate bone marrow aspirator device showing a handle, main housing, sleeve which translates along the axis of the needle, syringe body, syringe plunger and hand crank.
Figure 13:
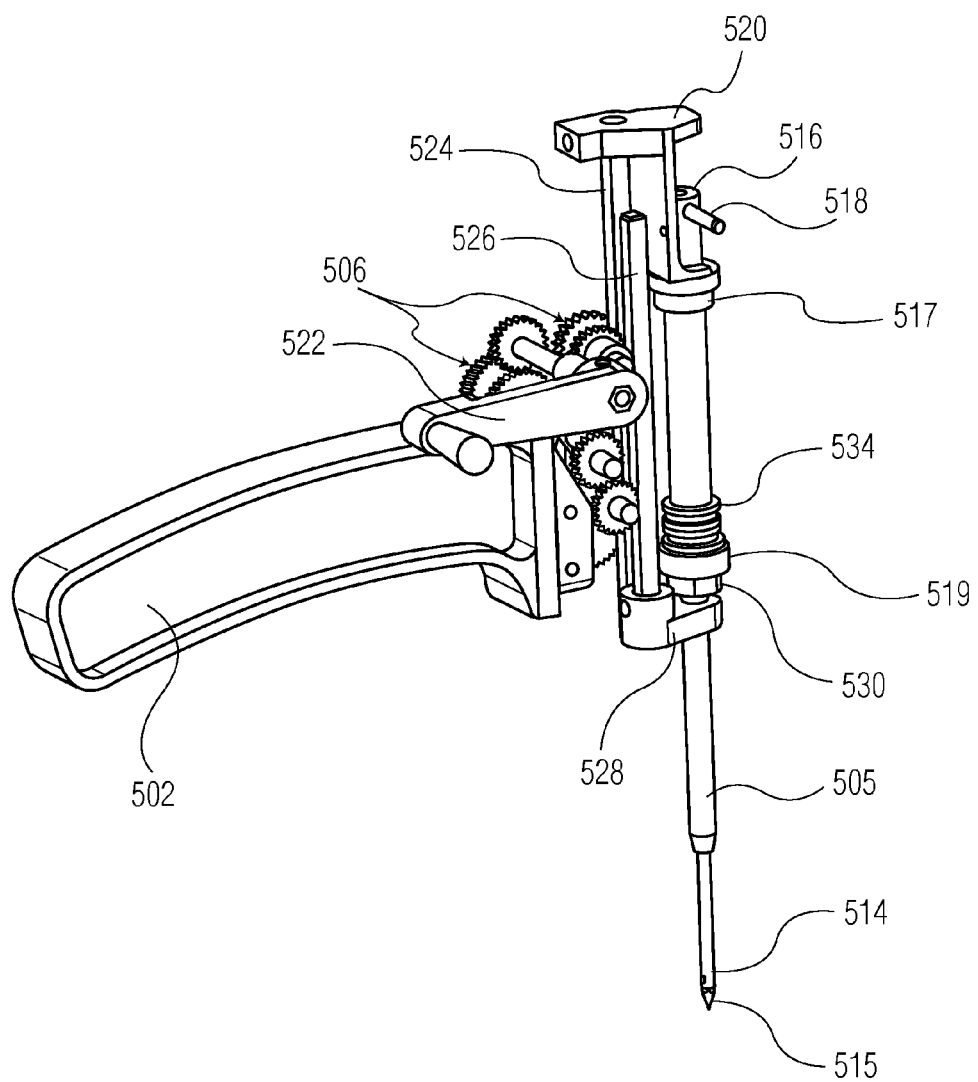
FIG. 13 is a second perspective view of the bone marrow aspirator of FIG. 12 with main housing removed for clarity purposes.

Referring to FIGS. 12 and 13 there is shown an alternate bone marrow aspirator embodiment of the present invention generally denoted as 500. Aspirator 500 includes a handle 502 fixedly attached to a housing 504. Housing 504 houses a drive system, which, in the preferred embodiment is a gear system 506 as shown in FIG. 13 as will be described in greater detail below which is driven by a hand crank 522. Housing 504 has a pair of bushing 508 and 510 coupled to a syringe body 512. Syringe body 512 has a hollow needle 514 fixed on needle housing 519 at a first end in a standard manner and has a plunger 516 slidably mounted within an interior of the syringe body 512. Needle 514 is surrounded by a sleeve 505 which is fixed to needle housing 519. Needle 514 includes a sharp tip 515 capable of penetrating cortical bone and has three ports 557 spaced at 120° around the needle adjacent tip 515. The plunger 516 includes a cross pin 518 extending therethrough and a plunger bushing 517. A plunger fork 520 is coupled to plunger 516 and is capable of moving plunger 516 within syringe body 512.

Gear system 506 may be driven by hand crank 522. Gear system 506 includes first and second gear racks 524 and 526 respectively. First rack 524 is coupled to plunger fork 520 and moves plunger 516 when the hand crank 522 is operated in a clockwise direction. Second rack 526 is fixed to a sleeve 505 by flange 528 which surrounds needle 514. Rotation of hand crank 522 clockwise drives the gear system causing rack 524 to move plunger fork 520 upwardly and forces rack 526 downwardly with respect to the housing 504.

Figure 14:
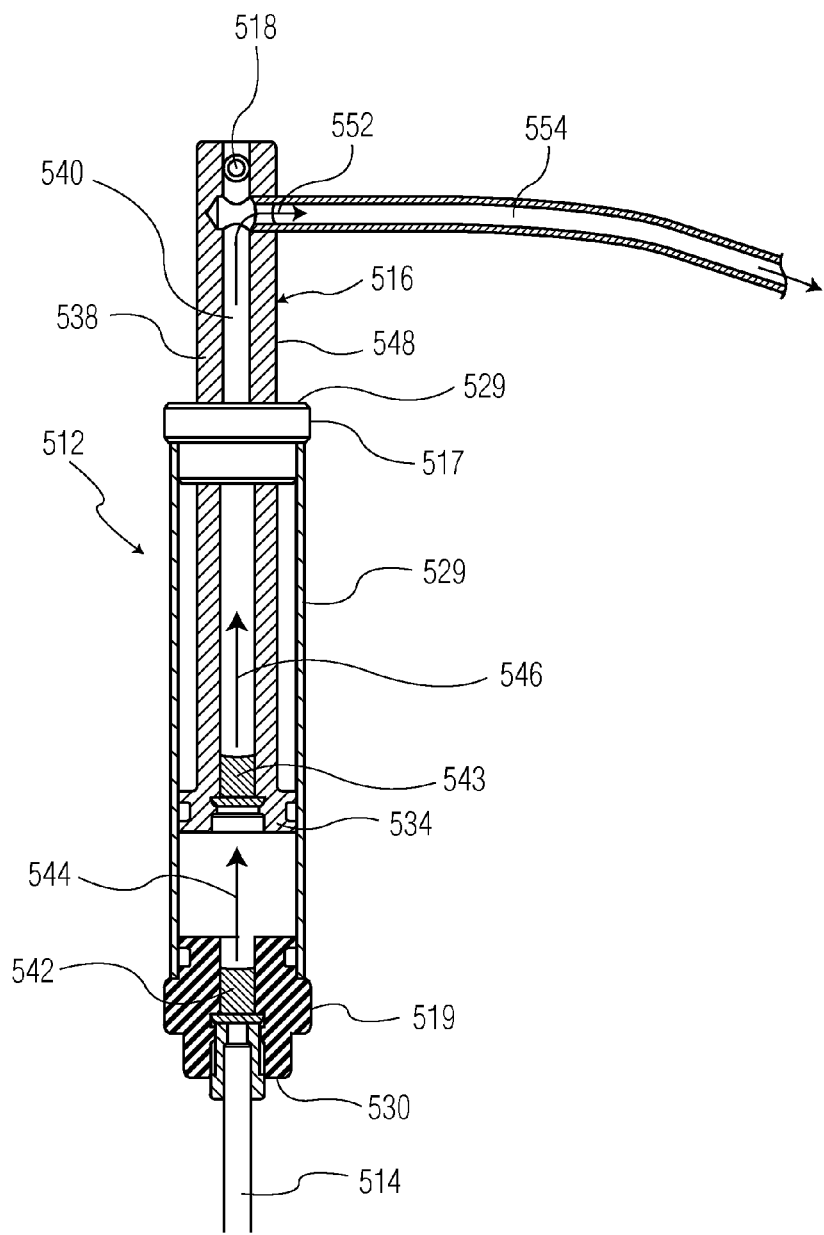
FIG. 14 is a cross sectional view of the syringe/plunger assembly shown in FIG. 12 along lines 14-14.

Referring to FIG. 14 there is shown a cross section of syringe body 512. Syringe body 512 comprises a barrel 529, a leading end 530 including a needle housing 519. Needle 514 is fixed to a leading end 530 of syringe body 512 in any standard manner within needle housing 519 fixed to end 530. A plunger piston 534 is mounted on a leading end 536 of a plunger shaft 538. Plunger shaft 538 is preferably a hollow cylinder with an internal flow path 540. Both needle housing 532 and plunger piston 534 includes first and second one way valves 542, 543 which allow fluid flow in the direction of the aspirate flowing from the needle into syringe barrel 529 (valve 542) though the syringe as indicated by arrows 544 and 546.

The trailing end of syringe barrel 529 includes a plunger bushing 517 which seals external shaft 548 of plunger 516. Cross pin 518 is mounted through a trailing end 549 of external surface 548 of plunger shaft 538. External shaft 538 is hollow and leads to an aspirate flow channel 550 which is in communication with flow path 540. Ports 552 extend from flow channel 550 to the external surface 548 of shaft 538 and into conduit 554. Conduit 554 carries the aspirate to a collection reservoir (not shown). First and second one way valves 542, 543 are typical rubber valves which prevent flow out of needle 514.

Figure 15:
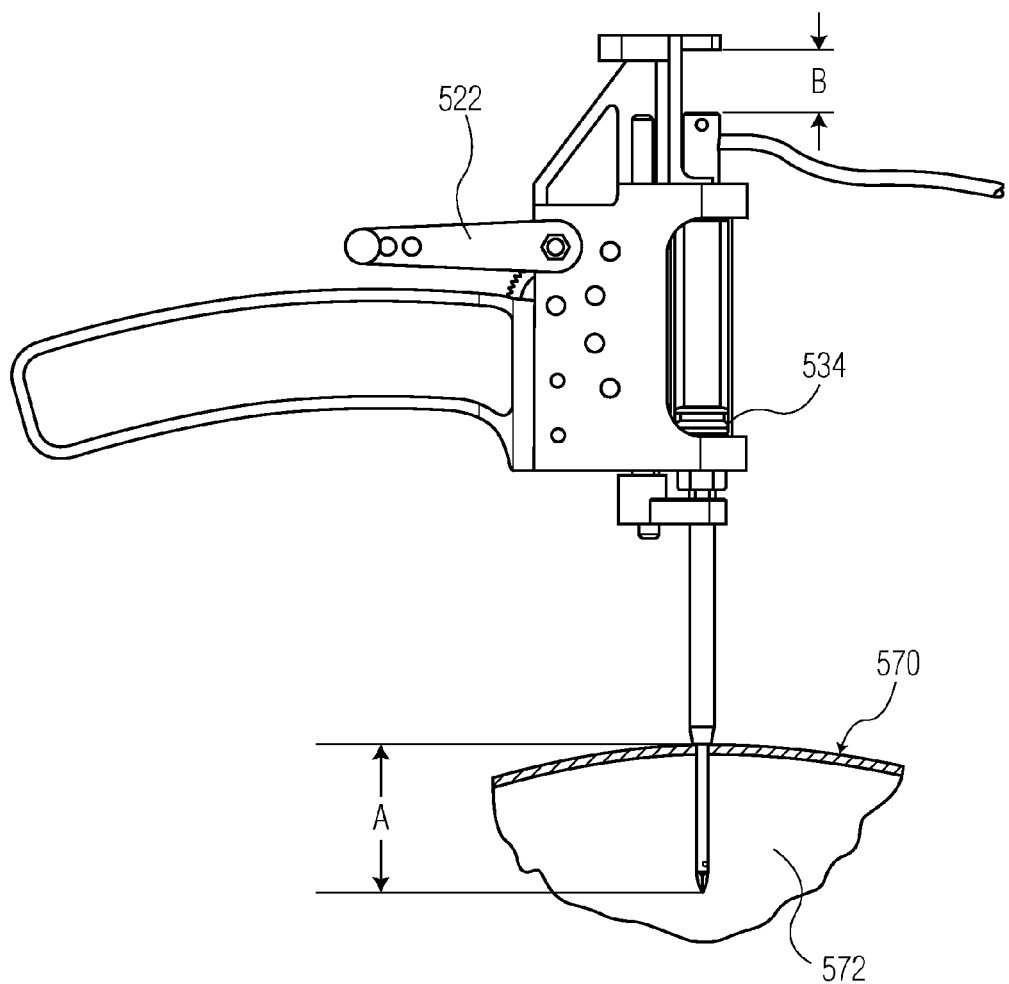
FIGS. 15-19 show the various steps in using the bone marrow aspirator of FIGS. 12-14.

The invention eliminates the variability inherent with the current manual process by automating the procedure to control aspiration volume with respect to needle location. The alternate embodiment operates in the following manner:

Step 1: As shown in FIG. 15, needle 514 is inserted into bone, for example, the iliac crest until the sleeve 505 makes contact with the cortex 570 resulting in a predetermined penetration depth of needle 5'4 into cancellous bone 572 shown as dimension "A".

Figure 16:
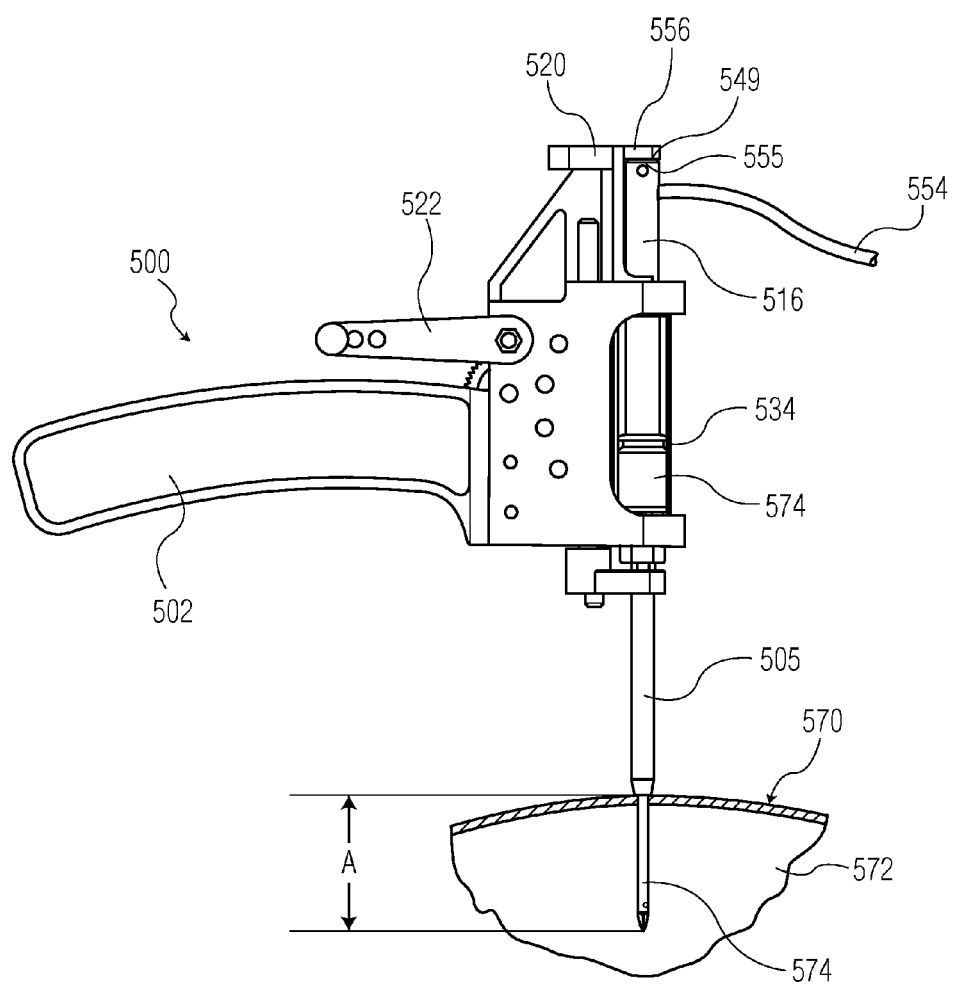
Figure 17:
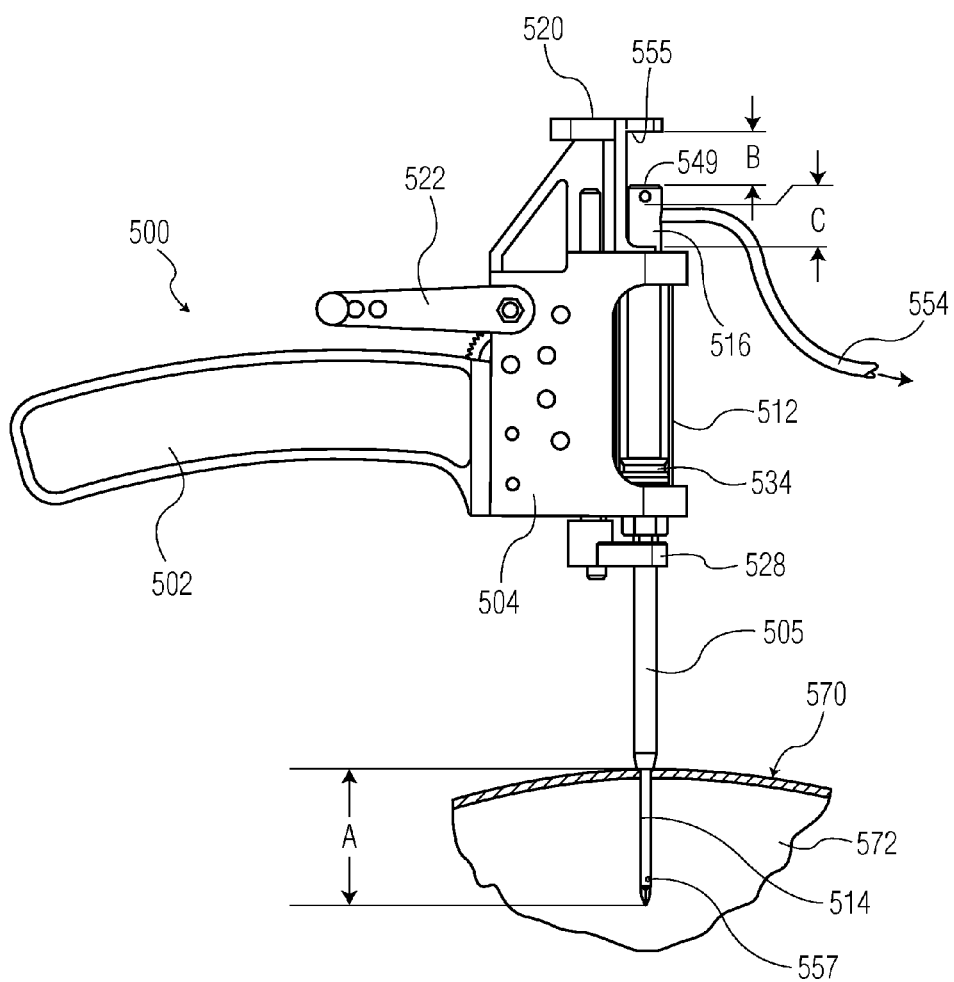

Step 2: As shown in FIG. 16, an initial volume of narrow aspiration 514 is collected from this site by pulling on the plunger cross pin 518 until a syringe plunger 516 upper end 549 bottoms out against a bottom surface 555 of upper tab 556 of the plunger fork 520. As shown in FIG. 17 the syringe plunger piston 534 can only travel a maximum distance "B" which is calculated to yield a maximum aspiration volume of about 2 ccs at initial depth "A" of needle 514.

Step 3: As shown in FIG. 17, the syringe plunger piston 534 is then returned to its initial position resulting in distance "B" once again being established between the syringe plunger end 549 and the under surface 555 of plunger fork 520. The initial bone marrow aspirate volume is evacuated through one-way flow valve 542 in needle housing 532 and through the central bore flow path 540 in the shaft portion of the syringe plunger shaft 538, through tube 554 and ultimately into a collection canister (not shown). One-way valves 542, 543 work such that during retraction of the plunger to create a vacuum pressure, valve 542 is open and 543 is closed. Reversing the plunger direction results in the closing of valve 542 and the opening of valve 543.

Figure 18:
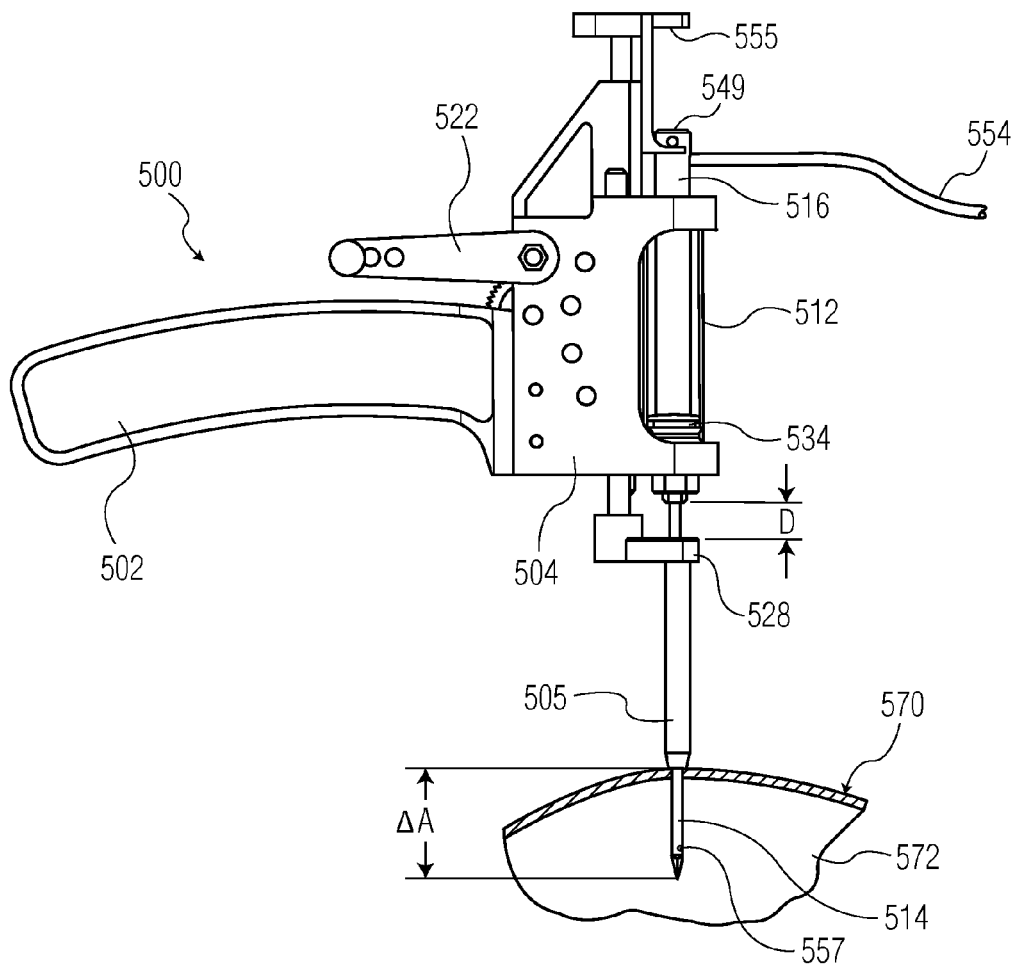

As shown in FIG. 18, the hand crank 522 is continued to be turned causing the gear drive to displace gear racks 524, 526 in opposite directions along the longitudinal axis of both gear racks. Gear rack 524 is coupled to plunger fork 520 and gear rack 526 is coupled to sleeve 505. The sleeve 505 extends a predetermined distance, referred to as distance "D", causing the needle 514 to retract from the bone by the same amount. The clearance between the plunger fork bottom surface 555 and the plunger cross pin 518, referred to as distance "C", enables needle 514 to be retracted proximally towards the cortical shell without any movement of the syringe plunger piston 534. Only when distance "C" is 0.00", will the syringe plunger piston 534 be engaged for continuous retraction. Distance "C" and "D" are the same therefore, after the initial aspiration of 2 ccs at depth "A", no further aspiration takes place between depths "A" and depth "ΔA".

Figure 19:
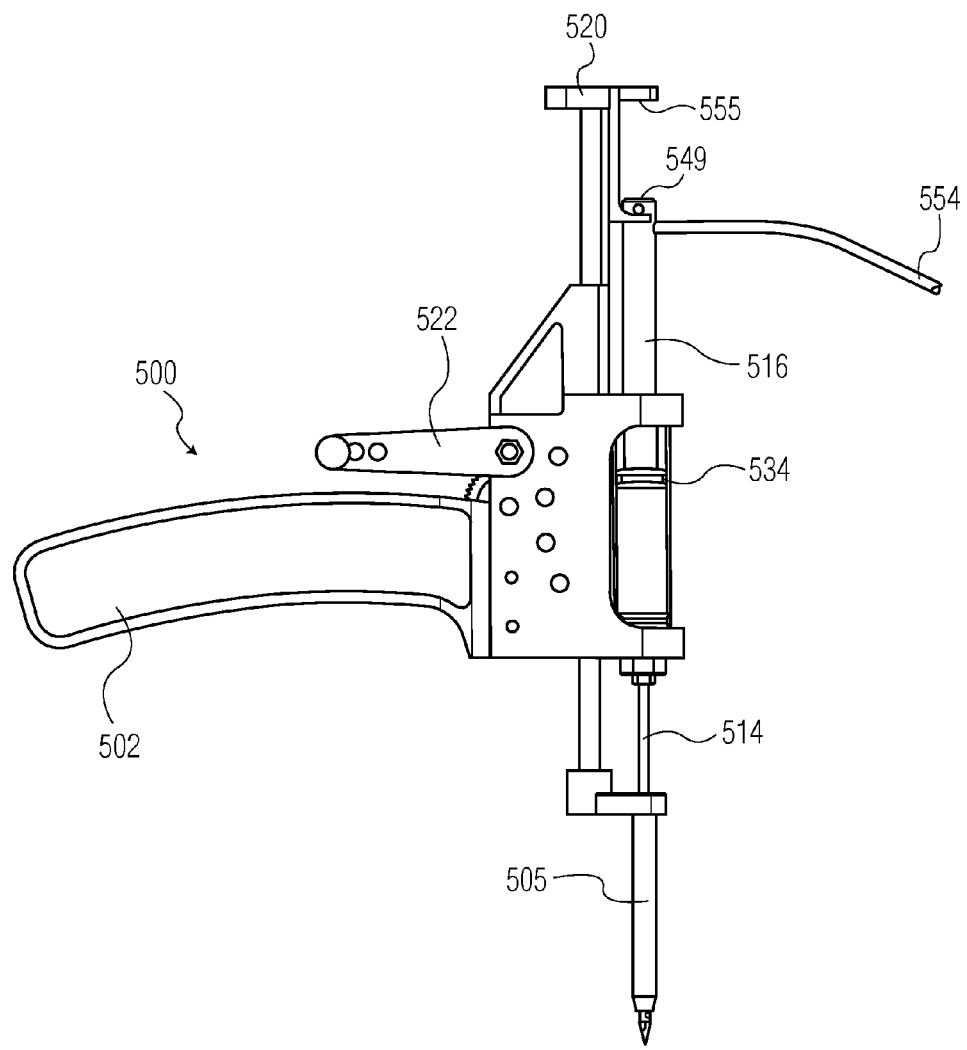

As shown in FIG. 19, as the crank 522 continues to be turned, the syringe plunger 534 and needle sleeve 505 extend in opposite directions at a fixed ratio of linear travel. This ratio ensures that at any 10 mm interval of needle 514 travel, the syringe plunger piston 534 displaces the required distance to collect 2 cc of bone marrow. Additionally, the three side ports 557 at the distal end of needle 514, which are spaced 120° apart from one another, assist in collecting marrow from a circumferential region adjacent to the tip of the needle 515.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A bone marrow aspirating device comprising:
a housing;
a reversible fluid pump mounted on the housing, the pump having an first port and a second port;
a fluid reservoir connected to the first port of the pump;
a moveable needle having a passageway therethrough mounted in the housing and connected to the second port of the pump, the needle having a drive system for moving the needle into and out of the housing;

an axially extending rotary input shaft connected to the pump and selectively engagable with the drive system for the moveable needle to move the needle with respect to the housing, the input shaft having a first axial position in which it drives the pump in a first direction to move fluid from the reservoir through the passageway of the needle but is disengaged from the needle drive system, a second axial position in which it drives the pump in a second direction to move fluid from the needle passageway to the second port but is disengaged from the needle drive system so that the needle does not move and a third position in which it drives the pump in the second direction to move fluid from the needle passageway to the second port and engages the needle to cause the needle to move with respect to the housing; and a selector switch having at least one of a first position and a second position preventing engagement of the input shaft and needle drive system and a third position allowing engagement of the input shaft and needle drive system for moving the needle with respect to the housing.

2. The device of claim 1, wherein the selector switch has a first position allowing an anticoagulant fluid to be pumped from the reservoir through the passageway in the needle; a second position for aspirating bone marrow without moving the needle; and a third position for withdrawing the needle while simultaneously aspirating bone marrow.

3. The device of claim 2, wherein in the third position, the needle is displaced proportionally to displacement of the volume in the reservoir.

4. The device of claim 3, wherein the drive system input shaft has an input gear thereon selectively engagable with a drive gear for moving the needle with respect to the housing, the proportional displacement is determined by the gear ratio of the drive gear to the input gear.

5. The device of claim 4, wherein in the first axial position of the input shaft the drive gear is disengaged and the input gear can only rotate the pump.

6. The device of claim 4, wherein in the second axial position of the input shaft the drive gear is disengaged and the input gear can only rotate in a second direction.

7. The device of claim 2, wherein in the third position the drive gear is engaged and the input gear can rotate in the second direction.

8. The device of claim 3, further comprising a threaded shaft rotatably connected to the needle driven by the drive gear through threaded shaft having a shuttle threadably mounted thereon, the shuttle housing the needle.

9. The device of claim 8, further comprising an indicator for determining displacement of the needle.

10. The device of claim 9, wherein the indicator displaces in relation to movement of the shuttle caused by the rotation of the threaded shaft engaging the drive gear.

11. The device of claim 1, wherein the pump is a peristaltic pump.

12. The device of claim 1, wherein the needle can be displaced by the shuttle approximately 5 centimeters.

13. A method for aspirating bone marrow, comprising;
providing an aspirator including: a housing; a pump mounted on the housing; a sleeve mounted on the housing, a reservoir in fluid connection to the pump; a displaceable needle having a passageway therethrough in fluid connection to the pump; a rotateable rotary input element for driving the pump and displacing the needle; and a selector switch having a first, second, and third position;
placing the selector switch in a first position and rotating the rotary input element in a first direction to drive the pump in a first direction, move anti-coagulant from the reservoir through the passageway in the needle to flush the fluid path with the anti-coagulant;
delivering the needle into bone until the sleeve hits cortical bone inserting the needle to a desired location;
placing the selector switch in a second position and rotating the rotary input element in a second direction to drive the pump and aspirate bone marrow through the passageway in the needle; and
placing the selector switch in a third position and rotating the input element in the second direction to retract the needle and simultaneously actuate the pump in the second direction to aspirate bone marrow through the passageway in the needle and into the reservoir.

14. The method of claim 13, wherein the aspirator further includes an indicator that indicates how far the needle displaced.

15. The method of claim 13, wherein the needle includes a drive gear engagable with the input element and wherein when the selector switch is in the first position the rotary input element does not engage the needle drive gear.

16. The method of claim 15, wherein when the selector switch is in the second position a drive gear does not engage the rotary input element.

17. The method of claim 16, wherein when the selector switch is in the third position a drive gear engages the rotary input element.

18. The method of claim 17, wherein the needle displacement and a reservoir volume displacement are proportional.

19. The method of claim 18, wherein the rotary input element is an input gear and the proportionality is set by a gear ratio between the drive gear and in the input gear.

* * * * *